US010968444B2

(12) United States Patent
Tran et al.

(10) Patent No.: US 10,968,444 B2
(45) Date of Patent: Apr. 6, 2021

(54) METHODS FOR GENERATING BISPECIFIC FUNCTIONAL AGENTS

(71) Applicant: Abzyme Therapeutics LLC, Pottstown, PA (US)

(72) Inventors: Hiep Tran, West Chester, PA (US); Xiaole Chen, Exton, PA (US); Christine Mary Prokopowitz, Douglassville, PA (US); Rolf Swoboda, Upper Darby, PA (US); Ian White, West Chester, PA (US)

(73) Assignee: Abzyme Therapeutics LLC, Pottstown, PA (US)

( * ) Notice: Subject to any disclaimer, the term of this patent is extended or adjusted under 35 U.S.C. 154(b) by 341 days.

(21) Appl. No.: 16/031,533

(22) Filed: Jul. 10, 2018

(65) Prior Publication Data

US 2018/0334666 A1 Nov. 22, 2018

Related U.S. Application Data

(63) Continuation-in-part of application No. 15/986,025, filed on May 22, 2018, now Pat. No. 10,704,040.

(60) Provisional application No. 62/509,360, filed on May 22, 2017, provisional application No. 62/530,960, filed on Jul. 11, 2017.

(51) Int. Cl.

| | |
|---|---|
| ***C12N 15/10*** | (2006.01) |
| ***C07K 16/00*** | (2006.01) |
| ***C07K 16/28*** | (2006.01) |
| ***C07K 16/46*** | (2006.01) |
| ***C07K 16/22*** | (2006.01) |

(52) U.S. Cl.

CPC .......... *C12N 15/1037* (2013.01); *C07K 16/00* (2013.01); *C07K 16/005* (2013.01); *C07K 16/22* (2013.01); *C07K 16/2881* (2013.01); *C07K 16/468* (2013.01); *C12N 15/1044* (2013.01); *C07K 2317/14* (2013.01); *C07K 2317/31* (2013.01); *C07K 2317/515* (2013.01); *C07K 2317/522* (2013.01); *C07K 2317/569* (2013.01); *C07K 2317/64* (2013.01)

(58) Field of Classification Search

CPC ................................................ C12N 15/1037

See application file for complete search history.

(56) References Cited

U.S. PATENT DOCUMENTS

| | | | | |
|---|---|---|---|---|
| 9,365,846 | B2 * | 6/2016 | Shaheen | C07K 16/00 |
| 9,683,226 | B2 * | 6/2017 | Wang | C07K 16/00 |
| 2018/0334666 | A1 * | 11/2018 | Tran | C07K 16/005 |

OTHER PUBLICATIONS

Shaheen et al. 2013 "A dual-mode surface display system for the maturation and production of monoclonal antibodies in glyco-engineered Pichia pastoris." PLoS One 8: e70190 (Year: 2013).*

Doerner et al. (FEBS Letters 588 (2014) 278-287) (Year: 2014).*

U.S. Appl. No. 15/986,025, filed May 22, 2018 entitled "Triple-Mode System for Antibody Maturation, Surface Display and Secretion".

U.S. Publication No. 2017/0183645 published Jun. 29, 2017 entitled "Composition and Method for Diversifying Polypeptide Libraries".

* cited by examiner

*Primary Examiner* — Scott Long

(74) *Attorney, Agent, or Firm* — Moser Taboada

(57) ABSTRACT

The present invention provides a method for preparing a modular scaffold that can bind to a target antigen and a method for engineering a bispecific functional agent consisting of an existing polypeptide binder fused at its C-terminus with said modular scaffold.

17 Claims, 13 Drawing Sheets

Specification includes a Sequence Listing.

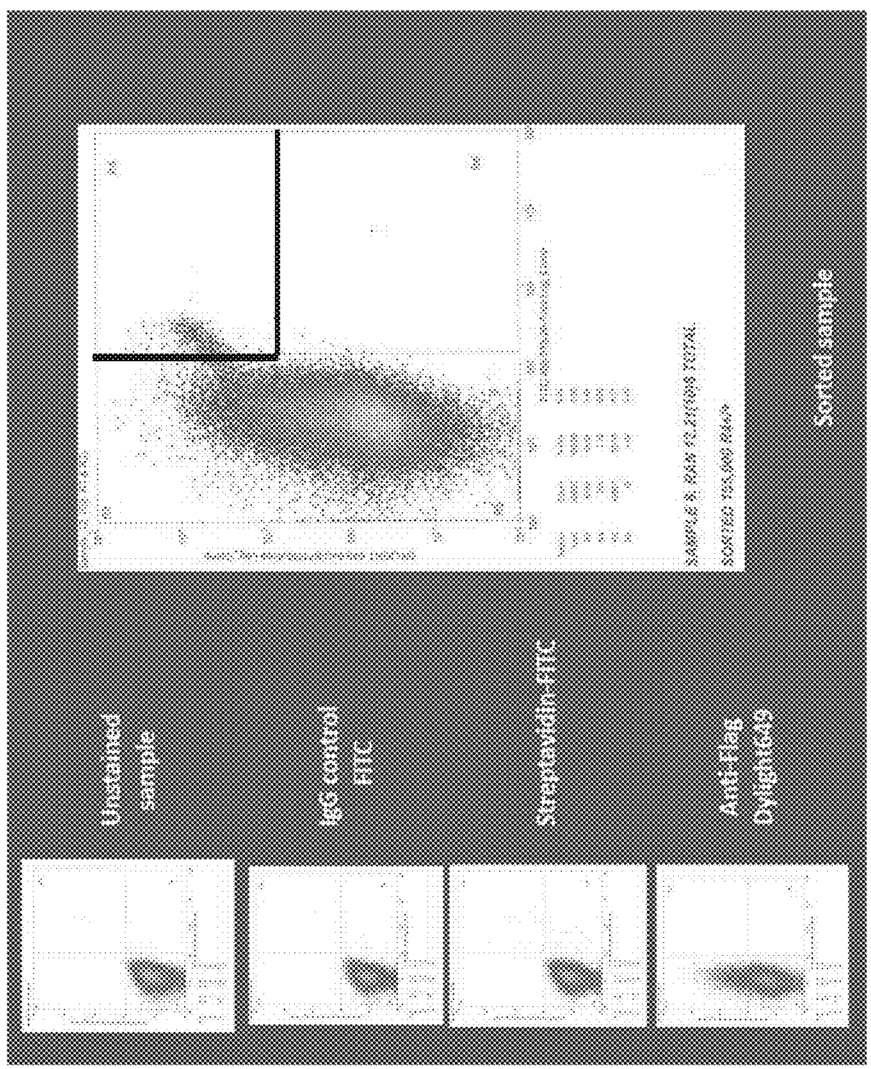
Figure 6. (need to replace this Figure with actual figure for TfR )

METHODS FOR GENERATING BISPECIFIC FUNCTIONAL AGENTS

CROSS-REFERENCE TO RELATED APPLICATIONS

This application is a continuation-in-part of U.S. Ser. No. 15/986,025, filed 22 May 2018 ("Triple-Mode System for Antibody Maturation, Surface Display and Secretion"), which claims the priority of U.S. Ser. No. 62/509,360, filed 22 May 2017 ("Triple-Mode System for Antibody Maturation, Surface Display and Secretion"), and further claims the priority of U.S. Ser. No. 62/530,960, filed 11 Jul. 2017 ("Methods for Generating Bispecific Functional Agents"), the contents of which are incorporated herein in their entirety.

FIELD OF THE INVENTION

The present invention relates generally to a polypeptide display system on a eukaryotic cell surface for identifying modular scaffolds with specific binding affinity to a target of interest applicable for generation of bispecific functional agents. The invention further relates to methods for generating bispecific functional agents.

SEQUENCE LISTING STATEMENT

Filed herewith is a Sequence Listing (name: ABZ002CIPSeqListing_25.txt, created: Jul. 10, 2018; sized: 67 KB). The content of that Sequence Listing is incorporated herein by reference in its entirety.

BACKGROUND OF THE INVENTION

In comparison with traditional antibodies, bispecific antibodies (BsAbs) offer a significant improvement in therapeutic index. The administered effective dose of bi-specific CD19/CD3 antibodies (Blinatumomab) is five orders of magnitude lower than the reported effective doses of the CD19-specific standard-of-care, Rituximab (Bargou et al. 2008; Choi et al. 2011). A strategy that harnesses the cytotoxic advantage of T cell therapy is to use of bispecific antibodies designed to engage and activate endogenous polyclonal T cell populations via the CD3 complex, but only in the presence of a tumor antigen (Choi et al. 2011). Bispecific T-cell engaging (BiTE) antibodies, bound to target cells are known to trigger cytotoxic activity of T-lymphocytes by crosslinking of CD3 (Mack et al. 1995; Perez et al. 1985; Staerz et al. 1985), irrespective of T-cell receptor specificity, major histocompatibility (MHC) restriction, or MHC down regulation on tumor cells (Pantel et al. 1991). A number of bi-specific antibodies are in clinical trials for cancer therapy such as bi-specific single chain Blinatumomab (CD19/CD3) and the rat-mouse hybrid monoclonal antibody Catumaxomab (EpCAM/CD3).

The use of bispecific antibodies has been hindered by difficulties in producing them in sufficient quantity and purity. Over the years, several technologies have been implemented in order to generate BsAb therapeutics: (i) rat/mouse quadroma technology (Atwell et al. 1997); (ii) chemical cross-linking (Doppalapudi et al. 2010; Jung et al. 1991), (iii) scFv-based formats (Huston et al. 1988); (iv) use of hetero-dimerization domains (Pack and Pluckthun 1992; Rossi et al. 2006); and (v) genetic engineering of the mAbs dimerization CH3 domain SEED (strand-exchange engineered domain) (Davis et al. 2010), "two-in-one" IgGs (Bostrom et al. 2009), "knob-in-hole" (Merchant et al. 1998; Ridgway et al. 1996), electrostatically steered bispecifics (Gunasekaran et al. 2010) and domain crossover (Schaefer et al. 2011). Other approaches such as engineering the IgG CH3 domain into a target antigen binding site (U.S. Pat. No. 9,255,149) are used. Two main limitations related to bispecific functional agents are manufacturability—(e.g. difficulties in large scale production of pure bispecific antibodies, aggregation caused by non-natural structure, heavy- and light-chain mispairing in the case of scFv); and poor pharmacokinetic and pharmacodynamics properties including immunogenicity, short serum half-life, or loss of Fc effector functions caused by the lack of the fragment crystallizable (Fc) region.

There therefore remains a great need for easily engineered bi-specifics with superior properties, like low immunogenicity and long half-life in humans that can be readily produced in high yield from mammalian cell culture while preserving the functional activity of the antibody components.

Single domain scaffold proteins including, but not limited to immunoglobulin heavy chain variable region and light chain variable region, Anticalins, Fibronectin type III domain, Designed Ankyrin Repeat Protein or Centyrin can serve as building blocks or modules for generating multispecific polypeptides simply via a linear fusion. The protein scaffolds alone normally function with free N-termini and therefore binding activity to the target antigen may be compromised when part of a multispecific fusion construct in which the N-terminus is no longer free. Pre-selection of functional target specific protein scaffolds with occupied N-termini would ensure its binding integrity after subsequent fusion to the C-terminus of existing antibodies. The present invention provides a means to select N-terminus-occupied functional single domain protein scaffolds that will remain functional when fused to the existing protein binders at the binder's C-terminus.

Biophysical properties of antibodies such as expressibility/manufacturability are important attributes for downstream development of therapeutic antibodies. While both the human antibody phage display platform and the transgenic mouse with humanized immune system were developed over 20 years ago, the ratio of FDA-approved full human antibodies as of May 2017 is 6:17 in favor of product from humanized transgenic mice. It is believed that phage-derived antibodies suffer from a higher frequency of biophysical property issues that create barriers to "developability" of these antibodies. These suboptimal attributes can lead to difficulties in pharmacokinetics (PK) (like accelerated clearance, limiting time "on target"), safety, and Chemistry, Manufacturing, and Control (CMC) issues. The present invention provides a eukaryotic expression system to select modular scaffolds with desired attributes such as expressibility and binding affinity, thereby improving the antibody "developability".

While single domain protein scaffolds such as human VH and camelid VHH can be developed in vivo using "humanized" mice or llamas, respectively, following immunization with a target antigen of interest, some potential confounding issues such as non-immunogenicity, self-antigen, or antigen toxicity may occur. In addition, the animal immune system is biased in the immune response to favor certain immunodominant epitopes, therefore resulting in epitope selection bias. The present invention provides an ex vivo animal-free system, therefore providing an unbiased epitope selection resulting in a broader epitopic diversity of selected antibodies.

In summary, advantages of this invention include the ability to isolate modular scaffolds that remain active when N-terminally fused, to select binders with desired therapeutic attributes, against difficult targets while providing larger epitopic diversity. In addition, the system is a low cost, rapid growth eukaryotic protein expression and surface display system with ease of culture and culture maintenance, facile manipulation and genetic engineering.

In an exemplary embodiment of the invention, a library of human or separately camelid VHs are fused to the C-terminus of the yeast outer membrane AGA2 protein (Uniprot number P32781, SEQ ID NO:7) for surface presentation.

In an embodiment of the invention expression of lamprey CDA1 (Uniprot number A5H718, SEQ ID NO:3)—the most powerful deaminase mutator of DNA in yeast, which in combination with the chemical supermutagen 6-N hydroxy amino purine or HAP—allows rapid library diversification. In an embodiment of the invention, the expression of any deaminase mutator allows rapid library diversification.

In an embodiment of the invention the use of diploid and/or polyploid yeast strains, in contrast to the normally used haploid yeast version, protects yeast cells from lethal mutation damage during the diversification stage, due to the presence of two or more copies of essential genes. Yeast cells expressing specific functional binders can be quickly identified using selection methods such as biological panning, Fluorescence Assisted Cell Sorting (FACS) for cell sorting or ELISA for secreted active antibody validation. Such methods can be used in combination.

SUMMARY OF INVENTION

The present invention provides methods and kits for diversifying and selecting N-terminus fused modular scaffolds with specific binding affinity to any target of interest and for engineering a bispecific functional agent consisting of an existing ligand-binding scaffold protein or polypeptide binder fused at its C-terminus with said modular scaffold. In a preferred embodiment, methods and kits for isolating N-terminus fused camelid single domain VHH antibodies (as scaffolds) are disclosed. In other embodiments, the cell-based self-diversifying methods are used to isolate N-terminus fused human heavy-chain only single domain antibodies. The cell-based self-diversifying platform has additional applications in diversifying other binders and maturating binders to modulate their functional activity. In another embodiment, a method of producing a bispecific functional binding agent is provided, wherein the bispecific functional binding agent consists of an existing polypeptide binder fused at its C-terminus with a selected modular scaffold of the invention, wherein the modular scaffold binds to a different target regardless of the target specificity of the polypeptide binder.

In an exemplary embodiment of the invention, human transferrin receptor (TfR) is presented as an antigen of interest. Genetically engineered host cells comprising a self-diversifying surface display N-terminus fused camelid VHH antibody library are then contacted with the antigen target. The engineered cells expressing antibodies reactive to the antigen are enriched by biological panning and isolated by Fluorescence-Activated Cell Sorting (FACS). Antibodies secreted from sorted cells are purified and confirmed for the target-specific binding activity.

In another embodiment of the invention, a cell-based system for N-terminus fused modular scaffold discovery is provided, wherein the system comprises a) a first DNA construct comprising a nucleic acid molecule encoding a prey polypeptide (e.g., yeast AGA2) fused at its C-terminus with a modular scaffold operably linked to a promoter; b) a second DNA construct having a nucleic acid molecule encoding a second polypeptide operably linked to a promoter; c) diversifying cell culture media supplemented with protein-expression inducer and mutation-causing chemicals; and d) two yeast strains of opposite mating types; the first yeast strain contains said first DNA construct; the second yeast strain contains said second construct; the final host cell is formed by mating the first and the second yeast strains comprising said first and second DNA constructs, diversification of said modular scaffold in said host cell being dependent upon enzymatic activity of said second polypeptide or the presence of the mutation-causing chemicals supplemented in said cell culture media.

In yet another embodiment, a method for isolating modular scaffold to a target of interest with modulated binding activity is provided, wherein the method comprises: a) providing a host cell containing a first DNA construct comprising a nucleic acid molecule encoding a prey polypeptide (e.g., AGA2) fused at its C-terminus with a modular scaffold operably linked to a first promoter; a second DNA construct having a nucleic acid molecule encoding a second polypeptide operably linked to a second promoter; and diversifying cell culture media supplemented with protein-expression inducers and mutation-causing chemicals; b) culturing said host cells in said diversifying media to diversify the said modular scaffold encoding genes; and c) isolating host cell expressing scaffold reactive to a target by either biological panning or FACS.

In a particular embodiment, the first DNA construct encodes a modular scaffold selected from the group consisting of immunoglobulin heavy chain or light chain variable regions or polypeptide scaffolds including, but not limited to Anticalins, fibronectin type III domain—Adnectins, Designed Ankyrin Repeat Protein or DARPins and Centyrins. In a particular embodiment, the second DNA construct encodes cytosine deaminases selected from group of sea lamprey cytosine deaminase 1 (PmCDA1), chimeric cytosine deaminase CDA2/CDA1 and their variants.

In yet another embodiment, a method for generating functional agents capable of binding two different target antigens is provided, wherein the method comprises: a) providing information for a nucleic acid molecule encoding a preexisting immunoglobulin or a protein scaffold specific for the first target, b) providing information for a nucleic acid molecule encoding a linker, c) providing information for a nucleic acid molecule encoding a modular scaffold selected as said above by screening for the ability to bind a different target d) synthesizing by recombinant construction or synthetic chemistry (or both) a DNA construct encoding the first protein scaffold, the linker and the selected modular scaffold operably linked to a promoter; e) introduction of the said DNA construct into a host cell; f) culturing said host cells; and g) purifying said recombinant bispecific agents.

In a particular embodiment, a bacterial vector containing two DNA constructs is used to express and produce in *E. coli* a VEGF×TfR bispecific agent consisting of a VEGF-binding antibody Fab fragment and an anti-TfR VHH scaffold. The first DNA construct encodes anti-VEGF antibody heavy chain fused at its C-terminus with anti-TfR VHH scaffold, the construct operably linked to a bacterial promoter. The second DNA construct encodes anti-VEGF antibody light chain operably linked to a bacterial promoter. In both DNA constructs, signal peptides for bacterial periplasmic expression are incorporated to the N-termini of the antibody polypeptides. Expressed heavy chain and light chain polypeptides transported into the cell periplasm form heterodimers stabilized by a disulfide bond. The dimers from the bacterial periplasm can be purified using affinity-resins such as protein G resins.

In a particular embodiment, a mammalian vector containing two DNA constructs is used to express and produce in HEK293 cells or other cell lines a VEGF×TfR bispecific agent consisting of a VEGF-binding antibody Fab fragment and an anti-TfR VHH scaffold. The first DNA construct encodes an anti-VEGF antibody heavy chain fused at its C-terminus with anti-TfR VHH modular scaffold operably linked to a mammalian cell promoter. The second DNA construct encodes an anti-VEGF antibody light chain operably linked to another mammalian cell promoter. In both DNA constructs, secretory signal peptides are incorporated in the N-termini of the polypeptides. Secreted Fab-VHH hybrid proteins can be purified using affinity-resins such as protein G resins.

DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only illustrative embodiments of this invention and are therefore not to be considered limiting of its scope, for the invention may admit to other equally effective embodiments.

FIG. 3A shows a replicative multicopy plasmid. FIG. 3B shows an integrative plasmid obtained from the plasmid presented in FIG. 3A by deleting the SnaBI-BsmBI region of the yeast 2-micron replication origin. Both yeast expression plasmids shown encode full-length lamprey cytosine deaminase 1 (PmCDA1). These yeast-*E. coli* shuttle plasmids contain LEU2 as a yeast transformation marker.

FIG. 6 shows graphs showing that the diversification and panning system of the invention efficiently sorts a cell population expressing camelid antibodies with high affinity binding to a target antigen. The enriched library is labeled with anti-HA Dylight649 and said antigen-biotin/streptavidin-FITC to monitor the VHH display efficiency and activity to said target, respectively. The double-positive sorted cell fraction is indicated.

FIG. 7A—Vector for expression of VEGF×TfR bispecific antibody in *E. coli; * FIG. 7B—Vector for expression of VEGF×TfR bispecific antibody in mammalian cells.

Figure 1:
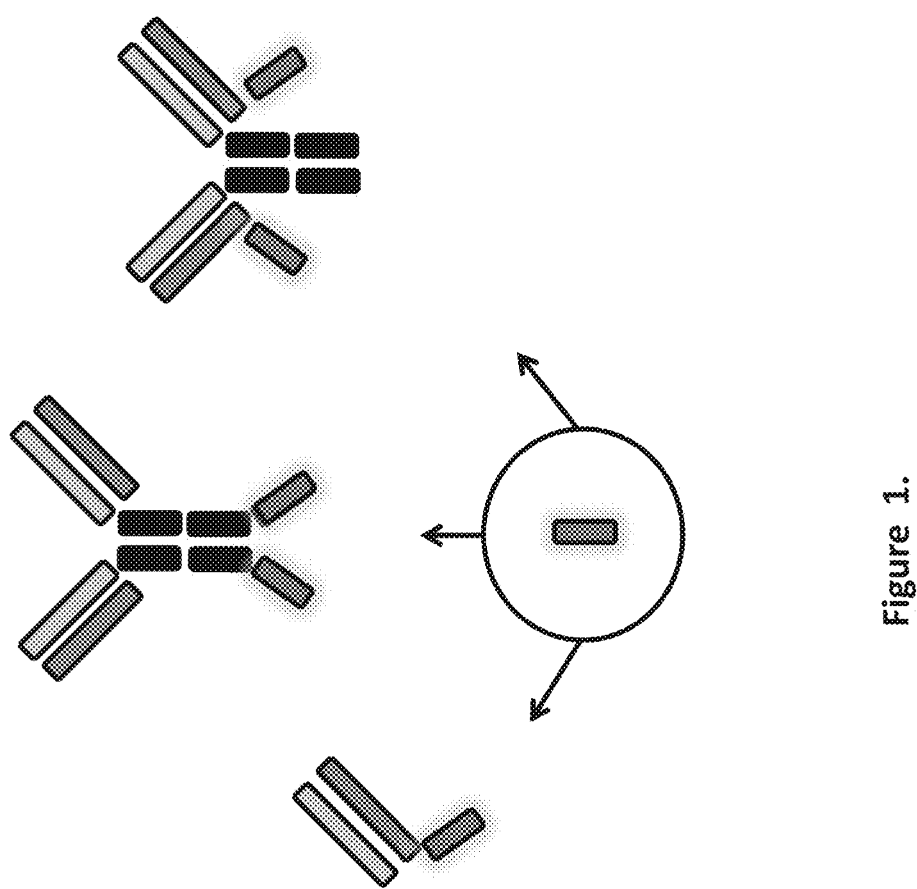
FIG. 1 presents several avenues for generating a bispecific functional agent consisting of an existing antibody (e.g., IgG or Fab fragment) and a modular scaffold pursuant to this invention. Modular scaffolds can be fused for example to the C-terminus of the light chain or to the C-terminus of antibody CH3 or CH1 domains.

To facilitate understanding, identical reference numerals have been used, where possible, to designate comparable elements that are common to the figures. The figures are not drawn to scale and may be simplified for clarity. It is contemplated that elements and features of one embodiment may be beneficially incorporated in other embodiments without further recitation.

DETAILED DESCRIPTION

In accordance with the present invention, compositions, methods and kits are provided for polypeptide diversification and isolation of a binder protein to a target of interest. A yeast-based system is disclosed to produce protein scaffolds reactive to a target. In a preferred aspect of the invention, an antibody discovery method is provided which enables isolating target-specific antibodies starting from a naïve antibody library.

A platform, with methods and tools, that can be used to effect the invention is the Triple-Mode System described in U.S. application Ser. No. 15/986,025, filed 22 May 2018, and U.S. Ser. No. 62/509,360, filed 22 May 2017 ("Triple-Mode System for Antibody Maturation, Surface Display and Secretion"). These applications are incorporated herein in their entirety. Further methods and tools that can be used to effect this invention can be found in U.S. patent application Ser. No. 15/380,105, filed 15 Dec. 2016, and U.S. application Ser. No. 62/387,511, filed 24 Dec. 2015 ("Composition and Method for Diversifying Polypeptide Libraries"). The content of this application is incorporated herein in its entirety.

I. DEFINITIONS

The following definitions are provided to facilitate an understanding of the present invention.

A "promoter" is a DNA sequence located proximal to the start of transcription at the 5' end of an operably linked transcribed sequence. The promoter may contain one or more regulatory elements or modules that act together in coordinating and regulating transcription of the operably linked gene. An inducible promoter is a promoter that responds to the presence of different biochemical stimuli. Such promoters include, but are not limited, to the CUP1 promoter, heat shock promoters, galactose-inducible promoters, glycolytic promoters such as alcohol dehydrogenase (ADH) glyceraldehyde phosphate dehydrogenase (GPD) and the like.

"Operably linked" describes two macromolecular elements arranged such that modulating the activity of the first element induces an effect on the second element. In this manner, modulation of the activity of a promoter element may be used to alter and/or regulate the expression of an operably linked coding sequence. For example, the transcription of a coding sequence that is operably linked to a promoter element can be induced by factors that "activate" the promoter's activity; transcription of a coding sequence that is operably-linked to a promoter element is inhibited by factors that "repress" the promoter's activity. Thus, a promoter region is operably linked to the coding sequence of a protein if transcription of such coding sequence activity is influenced by the activity of the promoter.

"Fusion construct" refers generally to recombinant genes which encode fusion proteins. Such fusion constructs may include operably linked nucleic acids isolated from two or more different genes.

"Modular" is relating to a module or modules as that serve as the basis of design or construction. Modular scaffold is an antibody that can serve as a building block in construction of a multispecific or multivalent fusion protein while retaining its binding activity.

A "fusion protein" is a hybrid protein, i.e., a protein that has been constructed to contain domains from at least two different proteins. An exemplary fusion protein, as described herein is a hybrid protein which possesses (a) a heavy chain VH-CH1 region of an anti-VEGF antibody (b) a single domain VHH antibody that binds to transferrin receptor. The term "fusion protein gene" refers to a DNA sequence that encodes a fusion protein. A fusion protein gene may further provide transcriptional and translational regulatory elements for the transcriptional and translational control thereof.

A nucleic acid molecule, such as a DNA or gene is said to be "capable of expressing" or "configured to express" a polypeptide if the molecule contains the coding sequences for the polypeptide operably linked to expression control sequences which, in the appropriate host environment, facilitate transcription, processing and translation of the encoded genetic information into a protein product.

The phrase "consisting essentially of" when referring to a particular nucleotide or amino acid means a sequence having the properties of a given reference sequence. For example, when used in reference to an amino acid sequence, the phrase includes the sequence per se and molecular modifications that would not affect the basic and novel characteristics of the sequence.

As used herein, a "cloning vector" is any entity that is capable of delivering a nucleic acid sequence into a host cell for cloning purposes. Examples of cloning vectors include plasmids or phage genomes. A plasmid which replicates autonomously in a host cell is especially preferred. Alternatively, a nucleic acid molecule which stably integrates into the host cell's chromosomal DNA and is inherited by daughter cells may be employed. Optionally, such vectors include a number of endonuclease recognition sites to facilitate manipulation of the sequence in a controlled and targeted fashion. Cloning vectors of the invention may also comprise sequences conferring resistance to selection agents, often referred to herein as selectable marker genes. For example, "a marker gene" may be a gene which confers resistance to a specific antibiotic on a host cell.

As used herein, an "expression vector" is a vehicle or vector similar to the cloning vector but is especially designed to provide an environment that facilitates expression of the cloned gene product after transformation of the vector into the host. Such vectors contain regulatory elements for expression in prokaryotic and/or eukaryotic hosts as well as sequences conferring selection properties of cells containing the expression vector. Optionally, enhancer elements, termination sequences, tissue-specificity elements, and/or translational initiation and termination sites may be included.

A "host" refers to any organism or cell line that is the recipient of a cloning or expression vector. In preferred embodiments, the host of the invention is a yeast cell or a cultured animal cell such as a mammalian or insect cell. Especially useful is the yeast host *Saccharomyces cerevisiae.*

A "transformed cell" is any cell into which (or into an ancestor of which) exogenous DNA has been introduced by means of recombinant DNA techniques or cell fusion, e.g. mating.

The terms "variant" or "derivative" in relation to lamprey CDA1 polypeptide includes any substitution of, variation of, modification of, replacement of, deletion of or addition of one (or more) amino acids from or to the polypeptide sequence of CDA1. Nucleic acids encoding CDA1 can comprise variants or derivatives thereof.

Such "modifications" of CDA1 polypeptides include fusion proteins in which CDA1 polypeptide or a portion or fragment thereof is linked to or fused to another polypeptide or molecule.

The term "homologue" as used herein with respect to the nucleotide sequence and the amino acid sequence of CDA1 may be synonymous with allelic variations in the CDA1 sequences and includes known homologues.

The "functional activity" of a protein in the context of the present invention describes the function the protein performs in its tested environment. Altering or modulating the functional activity of a protein includes within its scope increasing, decreasing or otherwise altering the native activity of the protein itself. In addition, it also includes within its scope increasing or decreasing the level of expression and/or altering the intracellular distribution of the nucleic acid encoding the protein, and/or altering the intracellular distribution of the protein itself. By "cytosine deaminase mutation activity" or "mutator activity" is meant the functional activity of cytosine deaminase or its homologues to increase the mutation rate above the background rate that occurs in the absence of the enzyme.

The term "expression" refers to the transcription of a gene's DNA template to produce the corresponding mRNA and translation of this mRNA to produce the corresponding gene product (i.e., a peptide, polypeptide, or protein). The tem "activates gene expression" refers to inducing or increasing the transcription of a gene in response to a treatment where such induction or increase is compared to the amount of gene expression in the absence of said treatment. Similarly, the terms "decreases gene expression" or "down-regulates gene expression" refers to inhibiting or blocking the transcription of a gene in response to a treatment and where such decrease or down-regulation is compared to the amount of gene expression in the absence of said treatment.

A wide variety of proteins have been subject to random mutation procedures to generate proteins that selectively bind substances. Those of skill will recognize such "scaffolds" (proteins) with a reasonable potential for generating such binding. As with many antibodies, scaffolds can be composed of subunit proteins. Scaffolds that have been used in the past include without limitation immunoglobulin heavy chain or light chain variable regions, combinations of light and heavy chains including Fab fragments, Anticalins, fibronectin type III domain (e.g., Adnectins), Designed Ankyrin Repeat Protein (DARPins), Centyrins, and the like.

A "scaffold library" is a library of genetically diverse scaffolds. For example, the library can encode Adnectins.

A surface, such as for example in a polystyrene multititer plate, has a substance "bound" thereto if its association with the surface is strong enough to allow cell panning. The binding can be, but is not necessarily, covalent.

A "bait" polypeptide binds a "prey" polypeptide with sufficient binding affinity so that they can form a dimer. The dimer may be further stabilized by disulfide bond(s) between the "bait" polypeptide and the "prey" polypeptide. The "prey" polypeptide is a polypeptide fused with a scaffold protein, while the "bait" polypeptide is either fused with a cell membrane anchor or without a cell membrane anchor.

Membrane anchored proteins include proteins located on the surface of the cell membrane that are covalently attached to lipids embedded within the cell membrane or cross the cell membrane. Overall, there are three main types of lipid-anchored proteins which include prenylated proteins, fatty acylated proteins and glycosylphosphatidylinositol-linked proteins (GPI). An example of yeast membrane anchored protein is AGA1—anchorage subunit of a-agglutinin of a-cells ("a" mating type) (Uniprot number P32323, SEQ ID NO:8); highly O-glycosylated protein with N-terminal secretion signal and C-terminal signal for addition of GPI anchor to cell wall, linked to adhesion subunit Aga2p via two disulfide bonds. Other yeast anchored proteins include CWP1, SED1, GAS1 and TIP1 (Kim et al. 2002). Examples of mammalian cell GPI-anchored proteins are GPI-proteins include cell surface receptors (e.g., folate receptor, CD14), cell adhesion molecules (e.g., NCAM isoforms, carcinoembryonic antigen variants, fasciclin I), cell surface hydrolases (e.g., 5'-nucleotidase, acetylcholinesterase, alkaline phosphatase), complement regulatory proteins (e.g., decay accelerating factor (CD55)) (Orlean and Menon 2007).

A dimer is a macromolecular complex formed by two, usually non-covalently bound, macromolecules such as proteins or nucleic acids. A homodimer is formed by two identical molecules (a process called homodimerization). A heterodimer is formed by two different macromolecules (called heterodimerization). The dimer may be further stabilized by a disulfide bond between the two macromolecules.

A disulfide bond, also called an S—S bond, or disulfide bridge, is a covalent bond derived from two thiol groups. In proteins, these bonds form between the thiol groups of two cysteine amino acids. These bonds are responsible for the stabilizing the globular structure and are the strongest type of bond that a protein can possess intrinsically and are one of the major forces responsible for holding proteins in their respective conformations, and therefore have an important role in protein folding and stability.

The "mutation rate" is the rate at which a particular mutation occurs, usually given as the number of events per gene per generation whereas "mutation frequency" is the frequency at which a particular mutant is found in the population.

"Hypermutation" or "increased mutation rate" or "increased mutation frequency" refers to the mutation of a nucleic acid in a cell at a rate above background. Preferably, hypermutation refers to a rate of mutation of between $10^{-5}$ to $10^{-3}$/base/generation. This is greatly in excess of background mutation rates, which are of the order of $10^{-9}$ to $10^{-10}$/base/generation (Drake et al. 1998).

The term "constitutive hypermutation" refers to the ability of certain cell lines to cause alteration of the nucleic acid sequence of one or more specific sections of endogenous or transgene DNA in a constitutive manner, that is without the requirement for external stimulation. Generally, such hypermutation is directed. In cells capable of directed constitutive hypermutation, sequences outside of the specific sections of endogenous or transgene DNA are not subjected to mutation rates above background mutation rates. The sequences which undergo constitutive hypermutation are under the influence of hypermutation-recruiting elements, as described further below, which direct the hypermutation to the locus in question. Thus in the context of the present invention, target nucleic acid sequences, into which it is desirable to introduce mutations, may be constructed, for example by replacing V gene transcription units in loci which contain hypermutation-recruiting elements with another desired transcription unit, or by constructing artificial genes comprising hypermutation-recruiting elements.

As used herein, a "mutator strain" refers to a yeast strain having a higher than naturally occurring rate of spontaneous mutation. As used herein, "mutator gene" refers to a gene which inactivation or overexpression causes a higher than naturally occurring rate of spontaneous mutation. Culturing a host comprising a mutator gene will give rise to mutational events during genome replication. An example of "mutator gene" that can be used in the present invention is UNG1 encoding Uracil DNA-glycosylase required for repair of uracil in DNA formed by spontaneous or induced cytosine deamination. When uracil-DNA glycosylase (Ung-) is lacking, the deamination of cytosine becomes a significant source of mutations (Duncan and Miller 1980). Inactivation of UNG1 in yeast results in increased mutation rates (Mayorov et al. 2005b). Another example of "mutator gene" that can be used in the present invention is sea lamprey CDA1 encoding cytidine deaminase that induces cytosine deamination on single stranded-DNA in vivo. CDA1 is considered an "active mutator gene" as its overexpression causes a higher than naturally occurring rate of spontaneous mutation in the host (Rogozin et al. 2007). It has been shown that overexpression of cytosine deaminases in combination with inactivation of uracil-DNA glycosylase results in synergistic mutator effects (Mayorov et al. 2005a).

A "color marker" has optical density (in a frequency band) or fluorescence directly, has enzymatic activity that generates the same, or is adapted to selectively bind one or more substances (e.g., biotin) such that eventually in the binding tree substances directly have or enzymatically generate optical density or fluorescence.

The meaning for "identity" (or "homology") for polypeptides is as follows: Polypeptide embodiments (including as components of methods or yeast cell systems) further include an isolated polypeptide comprising a polypeptide having at least a 50, 60, 70, 80, 85, 90, 95, 97 or 100% identity to a polypeptide "Reference Sequence" (e.g. SEQ ID NOs: 3, 4, 5 or 6), wherein said polypeptide sequence may be identical to the Reference Sequence or may include up to a certain integer number of amino acid alterations as compared to the Reference Sequence, wherein said alterations are selected from the group consisting of at least one amino acid deletion, substitution, including conservative and non-conservative substitution, or insertion, and wherein said alterations may occur at the amino- or carboxy-terminal positions of the Reference Sequence or anywhere between those terminal positions, interspersed either individually among the amino acids in the Reference Sequence or in one or more contiguous groups within the Reference Sequence, and wherein said number of amino acid alterations is determined by multiplying the total number of amino acids in the Reference Sequence by the integer defining the percent identity divided by 100 and then subtracting that product from said total number of amino acids in the Reference Sequence, or:

$n_a < X_a-(x_a \cdot y)$, wherein $n_a$ is the number of amino acid alterations, $x_a$ is the total number of amino acids in the Reference Sequence, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may include a contiguous segment of sequence that is identical to the Reference Sequence, that may be 100% identical, or it may include up to a certain integer number of amino acid alterations as compared to the Reference Sequence such that the percent identity is less than 100% identity.

All ranges recited herein include ranges there between, and can be inclusive or exclusive of the endpoints. Optional included ranges are from integer values there between (or inclusive of one original endpoint), at the order of magnitude recited or the next smaller order of magnitude. For example, if the lower range value is 0.2, optional included endpoints can be 0.3, 0.4, . . . 1.1, 1.2, and the like, as well as 1, 2, 3 and the like; if the higher range is 8, optional included endpoints can be 7, 6, and the like, as well as 7.9, 7.8, and the like. One-sided boundaries, such as 3 or more, similarly include consistent boundaries (or ranges) starting at integer values at the recited order of magnitude or one lower. For example, 3 or more includes 4 or more, or 3.1 or more. If there are two ranges mentioned, such as about 1 to 10 and about 2 to 5, those of skill will recognize that the implied ranges of 1 to 5 and 2 to 10 are within the invention.

II. METHODS AND COMPOSITIONS FOR GENERATING BISPECIFIC FUNCTIONAL AGENTS

The present invention relates to the antibody discovery and engineering field and consists of three components: (i) a package that includes cell and DNA constructs for generation of modular scaffolds; (ii) methods for generating a modular scaffold that can be used as a building block of a multi-specific polypeptide; and (iii) the incorporation of selected modular scaffolds into existing polypeptide binders to generate bispecific functional agents.

Cost effective and accelerated methods for antibody discovery will have broad impact on developing diagnostic, research and therapeutic antibodies. Currently ex vivo non-mammalian approaches for generating antibodies such as phage display (Hawkins et al. 1992), yeast surface display (Boder and Wittrup 1997; Boder and Wittrup 2000), ribosome display (Hanes and Pluckthun 1997; He and Taussig 1997) RNA display (Reiersen et al. 2005), and mammalian cell display (Beerli et al. 2008) are not intrinsically capable of affinity maturation because they lack the capacity to effect somatic hypermutation. Methods that may be potentially useful for antibody discovery are set forth in Table 1.

TABLE 1

Comparison of Triple-Mode discovery platform with other technologies

| Technology (references) | Speed | Cost | In vivo Maturation | Antigen limitation | Ease of application |
|---|---|---|---|---|---|
| Applicant's Triple-Mode System | High | Low | Yes | No | Yes |
| Animal approach | Low | High | Yes | Yes | No |
| Phage display | Moderate | Low | No | No | No |
| Yeast Display | Moderate | Low | No | No | No |
| Ribosomal Display | Moderate | Low | No | No | No |
| Mammalian cell display | Moderate | Moderate | No | No | No |
| Mammalian cell display + AID | Moderate | Moderate | Yes | No | Yes |

Numerous techniques to generate antibodies were evaluated. As can be seen from Table 1 only Applicant's Triple-Mode System (which in in embodiments can be called the Self-Diversifying Antibody Library or SDALib) described herein meets the desired criteria of cost, speed, self-maturation, low antigen limitation and ease of application. While a number of in vitro techniques can generate antibody, for maturation they require additional steps including in vitro error-prone PCR and library sub-cloning. Antibody maturation by error-prone PCR followed by sub-cloning is easily doable if the antibody is expressed by a single gene such as in the single domain (human VH or camelid VHH) or in the single-chain variable fragment (scFv) formats. When antibodies consist of separate light and heavy chain genes, error-prone PCR sub-libraries have to be constructed for each antigen-specific clone to maintain heavy-light chain pairing. Otherwise random pairing of a light chain from one active antibody with a heavy chain from a different clone will not likely generate again a target-specific antibody.

Advantages of this invention include low cost, rapid growth eukaryotic protein expression and a surface display system with ease of culture, culture maintenance, facile manipulation and genetic engineering. The expression of sea lamprey CDA—the most powerful deaminase mutator in yeast- directed to a DNA target in combination with the chemical supermutagen HAP allows rapid library diversification, and the use of diploid and/or polyploid yeast strains protect yeast cells from detrimental genetic damage of the induced mutagenesis due to the presence of two or more copies of essential genes. In combination with Fluorescence Assisted Cell Sorting (FACS) yeast cells expressing functional binders can be quickly identified. Eukaryotic cell surface display in combination with FACS sorting allows selection of functional binders with therapeutic attributes such as target-specificity, target-binding affinity, cross-species reactivity and expressibility which are desired for downstream candidate development and manufacturing.

In accordance with the present invention, a C-terminus modular scaffold library, a yeast-based genetic system and methods of use, thereof are provided to facilitate discovery of modular scaffolds followed by generation of bispecific functional agents. The methods provided herein enable the rapid and efficient maturation and isolation of modular antibody clones to an antigen target of interest starting from a naïve modular antibody library or alternatively to improve the activity of a known protein, including existing antibodies.

III. PREPARATION OF NUCLEIC ACID MOLECULES ENCODING THE PROTEINS OF THE INVENTION AND USES THEREOF IN ASSAY METHODS AND KITS

A. Nucleic Acid Molecules

Nucleic acid molecules encoding the expression vectors of the invention may be prepared by two general methods: (1) They may be synthesized from appropriate chemical starting materials, or (2) they may be isolated from biological sources. Both methods utilize protocols well known in the art.

The availability of nucleotide sequence information, for the sea lamprey CDA1, as well as for AGA2 gene facilitates synthesis of DNA constructs containing such sequences. Synthetic oligonucleotides can be prepared by the phosphoramadite method employed in the Applied Biosystems 38A DNA Synthesizer or similar devices. The resultant construct can be purified according to methods known in the art, such as high performance liquid chromatography (HPLC). Long, double-stranded polynucleotides, such as a DNA molecule encoding a construct of the present invention, must be synthesized in stages due to the size limitations inherent in current oligonucleotide synthetic methods. Thus, for example, a 3 kilobase double-stranded molecule can be synthesized as several smaller segments of appropriate complementarity. Complementary segments thus produced can be ligated such that each segment possesses appropriate cohesive termini for attachment of an adjacent segment. Adjacent segments can be ligated by annealing cohesive termini in the presence of DNA ligase to construct the entire 3 kilobase double-stranded molecule. A synthetic DNA molecule so constructed can then be cloned and amplified in an appropriate vector. In alternative embodiments of the invention, the sea lamprey CDA1, yeast AGA2, yeast SUC2 secretory signal and camelid VHH genes can be substituted with similar genes with functional homology from other biological sources.

In alternative embodiments of the invention, the sea lamprey CDA1, yeast AGA1, AGA2 and yeast SUC2 secretory signal can be substituted with similar genes with functional homology from other biological sources. In the PmCDA1 example, suitable candidate genes for such substitution include, without limitation, lamprey cytosine deaminase mutated (modified or altered cytosine deaminases), derivatives such as a CDA1 hybrid with ER DNA binding domain (ER-DBD), which also has high mutator phentotype once expressed in yeast defective in Uracil-DNA glycosylase. In addition, one can replace PmCDA1 with cytosine deaminase from other species, including but not limited to human AID.

In the example of yeast AGA1 and AGA2 heterodimerized via disulfide bond formation in ER, they can be substituted with components of an extracellular disulfide-bridged homodimer (e.g., 10 kDa uteroglobin, Uniprot # Q9TS45) or heterodimer protein such as human IL-12 encoded by two separate genes, IL-12A (Uniprot # P29459) and IL-12B (Uniprot # P29460).

Yeast SUC2 secretory signal of the invention used for promoting protein secretion may be derived from different species not limited to *S. pombe* and *K. lactis.* It can be substituted with yeast alpha mating factor secretory signal that also functions as secretory signal.

Nucleic acid sequences encoding the components of the expression plasmids of the invention can be isolated from appropriate biological sources using methods known in the art. For example, RNA isolated from a mammalian or insect cell may be used as a suitable starting material for the generation of cDNA molecules encoding the different receptor proteins.

In accordance with the present invention, nucleic acids having the appropriate level of sequence homology with the protein coding region of the DNA molecules of the present invention may be identified by using hybridization and washing conditions of appropriate stringency. For example, hybridizations may be performed at 37° C. to 42° C. for at least six hours. Targets with greater than about 75% sequence identity would be observed using a hybridization temperature of 42° C. Such a sequence would be considered substantially homologous to the sequences of the present invention. That the sequence encodes an appropriately functional polypeptide can be confirmed with ordinary experimentation.

The nucleic acids of the invention may also be used as starting materials for the generation of sequence variants or truncation mutants of the nucleic acids of the invention using any number of synthetic and molecular biologic procedures well known in the art including, but not limited to, truncation at available restriction sites and site-directed mutagenesis techniques. Particular mutations may give rise to receptor proteins with altered characteristics such as increased or decreased ligand binding activity.

B. Fusion Proteins

In one embodiment of the invention, the modular scaffolds of the invention are expressed in yeast as fusion proteins with yeast membrane anchor protein AGA2 at their N-termini. The protein membrane anchor functions to retain secreted antibodies or polypeptides on the yeast cell surface (Boder and Wittrup 1997) therefore accessible to an antigen of interest located extracellularly.

In one embodiment of the invention, the VEGF×TfR bispecific antibody is formed as a heterodimer of recombinant heavy chain and light chain, wherein, recombinant heavy chain is a fusion protein consisting of a signal peptide for *E. coli* periplasmic expression OmpA, followed by anti-VEGF VH-CH1 antibody and modular anti-TfR VHH antibody amino acid sequences; wherein a recombinant light chain is a fusion protein consisting of a signal sequence for *E. coli* periplasmic expression PelB and anti-VEGF VL-Ck antibody amino acid sequences. The vector for expression of VEGF×TfR bispecific antibody in *E. coli* is presented in FIG. 7A.

In one embodiment of the invention, the VEGF×TfR bispecific antibody is formed as a heterodimer of recombinant heavy chain and light chain, wherein, recombinant heavy chain is a fusion protein consisting of a mammalian cell secretory signal peptide, followed by VEGF VH-CH1 antibody and modular anti-TfR VHH antibody amino acid sequences; wherein a recombinant light chain is a fusion protein consisting of a mammalian cell secretory signal and VEGF antibody light chain amino acid sequences. An exemplary vector for expression of VEGF×TfR bispecific antibody in mammalian cells is presented in FIG. 7B.

C. Assay Methods and Kits

In yet another embodiment of the invention, assays are provided wherein intact cells expressing a protein of interest are grown in cell culture media containing base analogue molecules and molecules to induce expression of cytosine deaminase. After a suitable time period, the diversification of a gene or protein of interest is measured. Such diversification of a gene or protein of interest may be quantitated in a number of ways. For example, such cell diversification systems may utilize a reporter system in which the production of the reporter signal is dependent on enzymatic or fluorescence or binding activity of the protein of interest. Numerous reporters may serve equally well in this application including but not limited to, beta-galactosidase, alkaline phosphatase, green fluorescent protein, antibody, protein scaffold and the like. Inactivation or activation of the gene of interest can be also measured as forward and reverse mutation rates. For example, mutation in the arginine permease encoding gene CAN1 confers resistance to canavanine (Lang and Murray 2008). The gene diversification level can be measured by Next Generation Sequencing. Furthermore, the methods of the invention may be practiced in bacterial, fungal, insect, avian, mammalian or plant cells. However, yeast-based cell systems are preferred due to low cost and the feasibility of growing yeast cells in plastic devices.

Assays for screening binders to a target of interest are also provided. Diversification of binders in the cell-based system may be followed by isolation of cells expressing modified binders reactive to a target by means of biological panning or fluorescence-activation cell sorting (FACS). Isolation of binders reactive to a target of interest can be performed as described previously (Chao et al. 2006). In another aspect, the invention includes kits to facilitate the use of the compositions and methods disclosed herein. Exemplary kits include the expression plasmids, yeast-based scaffold libraries and yeast strains of the invention, and/or variants thereof. Also provided are cell culture media, compounds and protocols for use of the compositions of the invention for the particular application and the necessary reagents to carry out the application are also provided. Such reagents may include, but not be limited to, buffers, solvents, media and solutions.

The following protocols are provided to facilitate construction of the expression plasmids for use in the methods and kits of the present invention.

Media, Strains, Plasmids, Antibody Library

Standard yeast and *E. coli* media were prepared as described in detail (Chao et al. 2006). For example, YPD composed of Yeast Extract (20 grams per liter), Peptone (20 g/liter), Dextrose (20 g/Liter) is preferred for use in the invention as most yeast strains grow in this media. Yeast selective media (complete-drop out) used to maintain plasmids is composed of yeast nitrogen base 1.7 g/L, ammonium sulfate 5 g/L, dextrose 20 g/L, different amino acids and other supplements depending on the requirements of the particular yeast strain. For example if the yeast plasmid contains the LEU2 marker, leucine is dropped out from the media in order to select the plasmid. Other buffered selective media such as SDCAA glucose media and SGRCAA galactose media were prepared as described in detail (Chao et al. 2006).

HEK293 cells (ATCC catalog number CRL-1573™) were cultured in DMEM and OPTI MEM I cell culture media (Thermofisher). Lipofectamine 3000 tranfection kit (Thermofisher) was used for DNA transfection into the HEK293 cell line. A modified pVITRO1 vector (Invivogen) containing DNA constructs encoding antibodies was used for expressing bispecific functional antibodies in mammalian cells.

Yeast strains suitable for use in the present invention include without limitation the yeast strains of opposite mating types A168: MatA ura3-52 trp1-Δ63 Gal1p-PmCDA1::LEU2 leu2 his3::zeo$^R$ pep4-3 prb1-22 prc1-407 ung1::HygB ham1::KanMX and A169: Mat Alpha Gal1pAGA1::URA3 ura352 trp1::NatMX leu2Δ200 his3Δ200 lys2Δ pep4::Zeo$^R$ prbΔ1.6R can1 ung1::HygB ham1::KanMX. The A168 yeast strain can contain the first DNA construct capable of expressing a mutagenic cytidine deaminase; the second yeast strain A169 can contain the second recombinant DNA construct capable of expressing a membrane-bound bait polypeptide (e.g., AGA1) and a recombinant DNA capable of expressing one or more scaffold polypeptides, with one or more said scaffold polypeptides operably fused to the C-terminus of a prey polypeptide (e.g. AGA2). Diploids formed as a result of mating A168 yeast strain with A169 strain carrying C-terminus modular antibody library will provide yeast cells competent for modular antibody generation.

Figure 2:
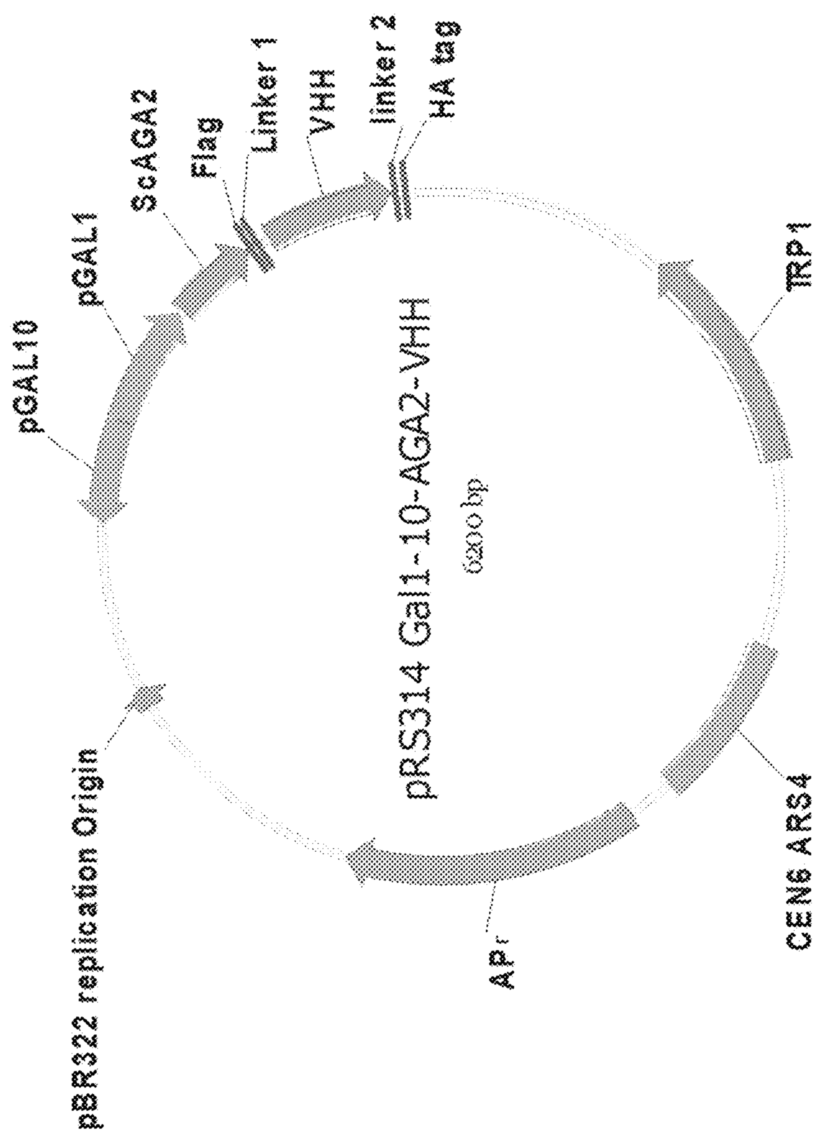
FIG. 2 is representative of one camelid VHH cloned in frame with a yeast outer membrane protein AGA2 at the VHH's N-terminus. A fusion AGA2-VHH library has been constructed using a transformation-associated gap repair approach as described (Weir and Keeney 2014). The fusion construct is expressed under a galactose inducible promoter, Gal1/10. This yeast-*E. coli* centromeric shuttle plasmid contains TRP1 as a yeast transformation marker.

A series of yeast expression plasmids for expression and display of a C-terminus modular antibody on the yeast cell surface were constructed based on the yeast-*E. coli* single copy plasmid pRS314 (Sikorski and Hieter 1989). All plasmids are yeast-*E. coli* centromeric shuttle plasmids containing TRP1 as a yeast transformation marker. FIG. 2 depicts an exemplary plasmid pRS314_Gal1/10p_AGA2_VHH of the invention that contains a gene encoding camelid heavy chain variable domains fused at the C-terminus of AGA2 for presentation on the yeast cell surface. Other scaffold proteins of interest that can be expressed and displayed on the yeast cell surface similar to the vector mentioned above include, but are not limited to human VH, Anticalins, Fibronectin type III domain—Adnectins, Designed Ankyrin Repeat Protein or DARPins and Centyrins.

Provided is a camelid C-terminus VHH library expressed in the yeast-*E. coli* expression vector pRS314-Gal1/10-AGA2-VHH (FIG. 2). Complementary DNA (cDNA) derived from camelid leukocyte mRNA encoding heavy chain variable domains was cloned in frame at its N-terminus with AGA2. cDNA library construction is well known in the art. The camelid VHH library was introduced into the A169 yeast strains using Trp$^+$ selection. The final self-diversifying camelid antibody library was obtained by mating the A169 library with the A168 yeast strain containing the chromosomally integrated CDA gene.

Also provided is a human C-terminus VH library constructed similarly as presented in FIG. 2. Complementary DNA (cDNA) derived from more than 500 human donor leukocyte mRNA samples encoding heavy chain variable domains was cloned in frame at its N-terminus with AGA2. The human VH library was introduced into the A169 yeast strains using $Trp^+$ selection. The final self-diversifying camelid antibody library was obtained by mating A169 library with the A168 yeast strain containing the CDA gene chromosomal integrated.

Diversification Methods

A diploid host cell containing a first DNA construct having a nucleic acid molecule encoding a protein that is subjected for diversification and a second DNA construct having a nucleic acid molecule encoding cytosine deaminase will undergo diversification by two means either performed separately or in combination.

In the first means of diversification a host cell containing constructs of the invention is continuously grown in yeast selective media that contains promoter inducers including but not limited to (1) galactose (20 g/L) as a sole carbon source to induce the Gal1/10 promoter or (2) copper at concentrations of 100 micro molar to 1 mM to induce the Cup1 promoter. Under such conditions cytosine deaminase is expressed. Produced cytosine deaminases will convert C to U via deamination in transcriptionally active genes including a gene of interest.

In the second means of diversification, a host cell containing constructs of the invention is continuously grown in yeast selective media containing base analogues including, but not limited to 6N-hydroxylamine purine or HAP. During replication the base analog 6-N-hydroxylaminopurine (HAP) induces bidirectional GC→AT and AT→GC transitions (Shcherbakova and Pavlov 1993).

As gene diversification occurs via hypermutation that is active during cell division via DNA replication, the level of diversification obtained is directly related to numbers of mutations in a gene of interest that accumulate as cells grow. Therefore the longer cells undergo diversification, the more mutations will accumulate.

Methods for Identifying Modular Scaffold to a Target of Interest

In an embodiment of the invention, after the diversification step, the eukaryotic host cells expressing the AGA2/antigen-binding modular scaffold complexed with anchored membrane protein AGA1 are identified and sorted using fluorescence-activated cell sorting (FACS). For example, in an embodiment of the invention, cells expressing the AGA2/antigen-binding modular scaffold fragment on the cell surface are labeled with either a fluorescent antigen or biotinylated antigen/fluorescent streptavidin. The fluorescent label is detected during the FACS experiment and used as the signal for sorting. Labeled cells indicate the presence of a cell surface expressed AGA1/AGA2/antigen-binding fragment/antigen complex and are collected in one vessel whereas cells without signal are collected in a separate vessel. The present invention, accordingly, includes a method comprising the following steps for determining if an antibody or antigen-binding fragment thereof from a library specifically binds to an antigen:

(1) Grow in a liquid culture media host cells comprising:
  (i) sea lamprey cytidine deaminase or functional fragment thereof;
  (ii) and one or more AGA2 fused antibody scaffolds;
  (iii) and membrane anchor AGA1 or functional fragment thereof;
(2) Allow expression of modular scaffolds and the anchored AGA1 on the surface of the cells;
(3) Optionally, enrich cells expressing binders to an antigen of interest with one or more rounds, with three rounds illustrated as follows:
  (i) Label cells with biotinylated antigen or any other antigen tag;
  (ii) Collect labeled cells using streptavidin-coated magnetic particles for one enrichment round or any other interacting magnetic particles;
  (iii) Regrow the labeled, enriched cells;
  (iv) Allow expression of antibody scaffolds and the anchored AGA1 on the surface of the cells;
  (v) Label cells with tagged antigen;
  (vi) Collect labeled cells using Avidin-coated magnetic particles for a second enrichment round.
  (vii) Regrow the labeled, enriched cells;
  (viii) Allow expression of antibody scaffolds and the anchored AGA1 on the surface of the cells;
  (ix) Label cells with biotinylated antigen;
  (x) Collect labeled cells using anti-biotin-coated magnetic particles for a third enrichment round
(4) Regrow the enriched cells (if step (3) conducted).
(5) Allow expression of antibody scaffolds and the anchored AGA1 on the surface of the cells (if steps (3) and (4) conducted);
(6) Label the cells with fluorescently labeled antigen or antigen bound to a fluorescently labeled secondary antibody;
(7) Sort and isolate fluorescently labeled cells using FACS for one round;
(8) Regrow the sorted cells;
(9) Optionally, allow expression of antibody scaffolds and the anchored AGA1on the surface of the cells and conduct a second round of (6)-(8);
(10) Regrow the labeled, sorted cells on solid culture medium so that individual cellular clones grow into discrete cellular colonies;
(12) Identify colonies with affinity for the antigen, such as using cytoflow analysis;
(13) Optionally, determine the nucleotide sequence of polynucleotides in the identified clones encoding the modular antibody.

Methods for Engineering Bispecific Functional Agents.

A bacterial host cell such as *E. coli* or eukaryotic host cells such as mammalian HEK293 can be used for expressing and producing a bispecific functional binding agent, wherein the bispecific functional binding agent consists of a ligand-binding scaffold protein fused at its C-terminus via a linker with a modular antibody, wherein the modular scaffold binds to a different target regardless of the target specificity of the scaffold protein, wherein the scaffold protein is an immunoglobulin heavy chain variable region, a light chain variable region, combinations of light and heavy chain regions, Anticalins, fibronectin type III domain, Designed Ankyrin Repeat Protein or Centyrin.

In one embodiment of the invention, the ligand-binding scaffold protein is anti-VEGF antibody Fab fragment and the modular scaffold is anti-TfR VHH isolated from the VHH modular scaffold library. VEGF×TfR bispecific antibody formed as a heterodimer of recombinant heavy chain and light chain, wherein, the recombinant heavy chain is a fusion protein consisting of the OmpA signal peptide for *E. coli* periplasmic expression, followed by anti-VEGF VH-CH1 and modular anti-TfR VHH antibody amino acid sequences; wherein a recombinant light chain is a fusion protein consisting of the PeIB signal peptide for *E. coli* periplasmic expression and anti-VEGF VL-Ck acid sequences. A exemplary vector for expression of VEGF×TfR bispecific antibody in *E. coli* is presented in FIG. 7A.

In one embodiment of the invention, the VEGF×TfR bispecific antibody formed as a heterodimer of recombinant heavy chain and light chain, wherein, recombinant heavy chain is a fusion protein consisting of a mammalian cell secretory signal peptide, VEGF antibody VH-CH1, and modular anti-TfR VHH antibody; wherein a recombinant light chain is a fusion protein consisting of a mammalian cell secretory signal peptide and VEGF antibody light chain. The vector for expression of VEGF×TfR bispecific antibody in mammalian cells is presented in FIG. 7B.

The present invention, accordingly, includes a method comprising the following steps for engineering bispecific functional agents consisting of a ligand-binding scaffold protein and modular antibody:

a) selection of appropriate expression host e.g., *E. coli* or mammalian cells
b) synthesis of DNA constructs encoding recombinant protein consisting of a given polypeptide binder and a selected modular antibody wherein the polypeptide binder is fused at its N-terminus with a secretory signal peptide that is functional in the given host for protein secretion, wherein the selected modular antibody is fused to the C-terminus of the given polypeptide binder, wherein the DNA construct is operably linked to a promoter that is functional in the selected host
c) introduction of the DNA construct into the host cells
d) Culturing the host cells such that the recombinant protein encoded by the DNA construct is expressed.

Protein purification as well as antibody characterization by various immunoassays such as ELISA, Western blotting or cytoflow analysis are well known in the art.

Figure 3B:
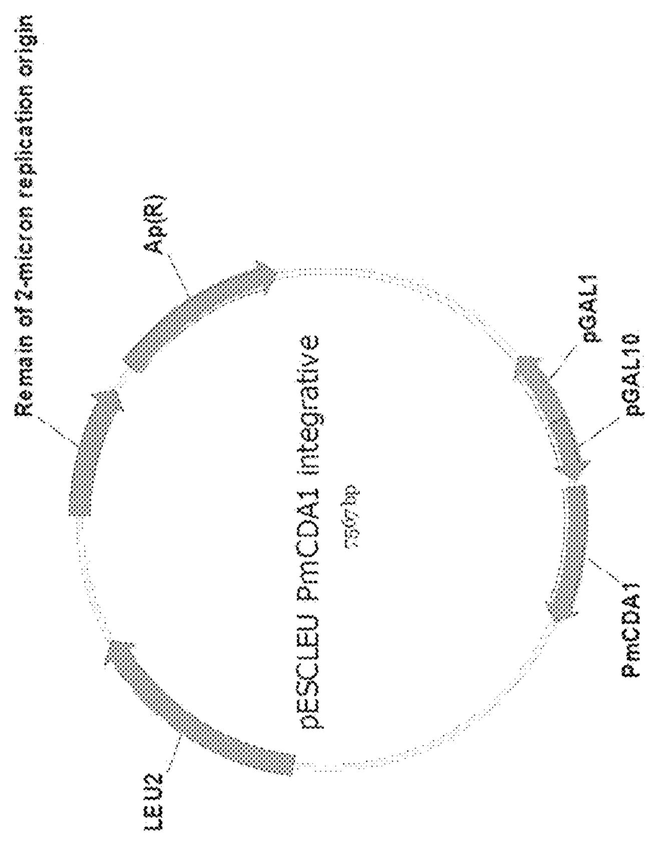
FIGS. 3A and 3B present vectors for expressing the second polypeptide constructs.
Figure 3A:
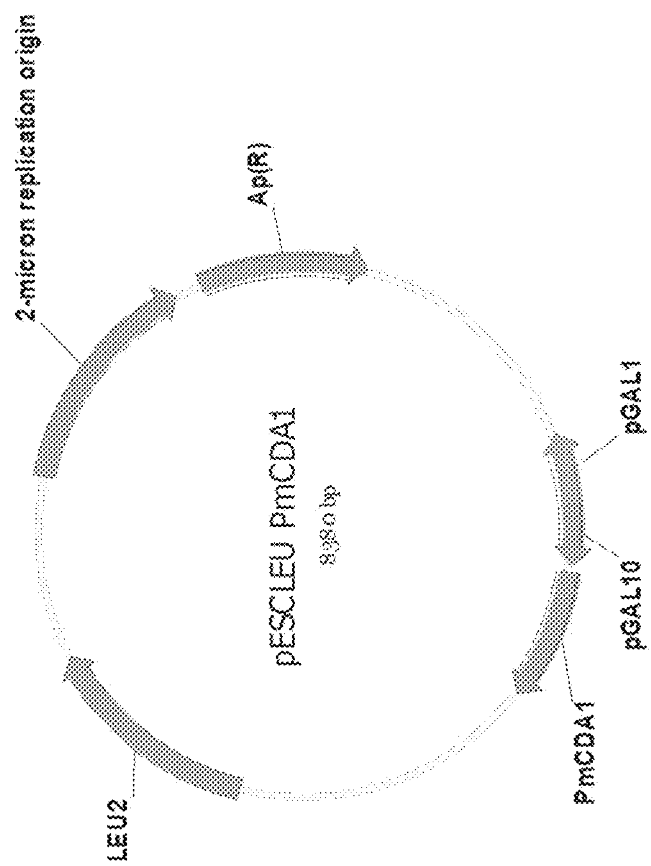
Figure 3C:
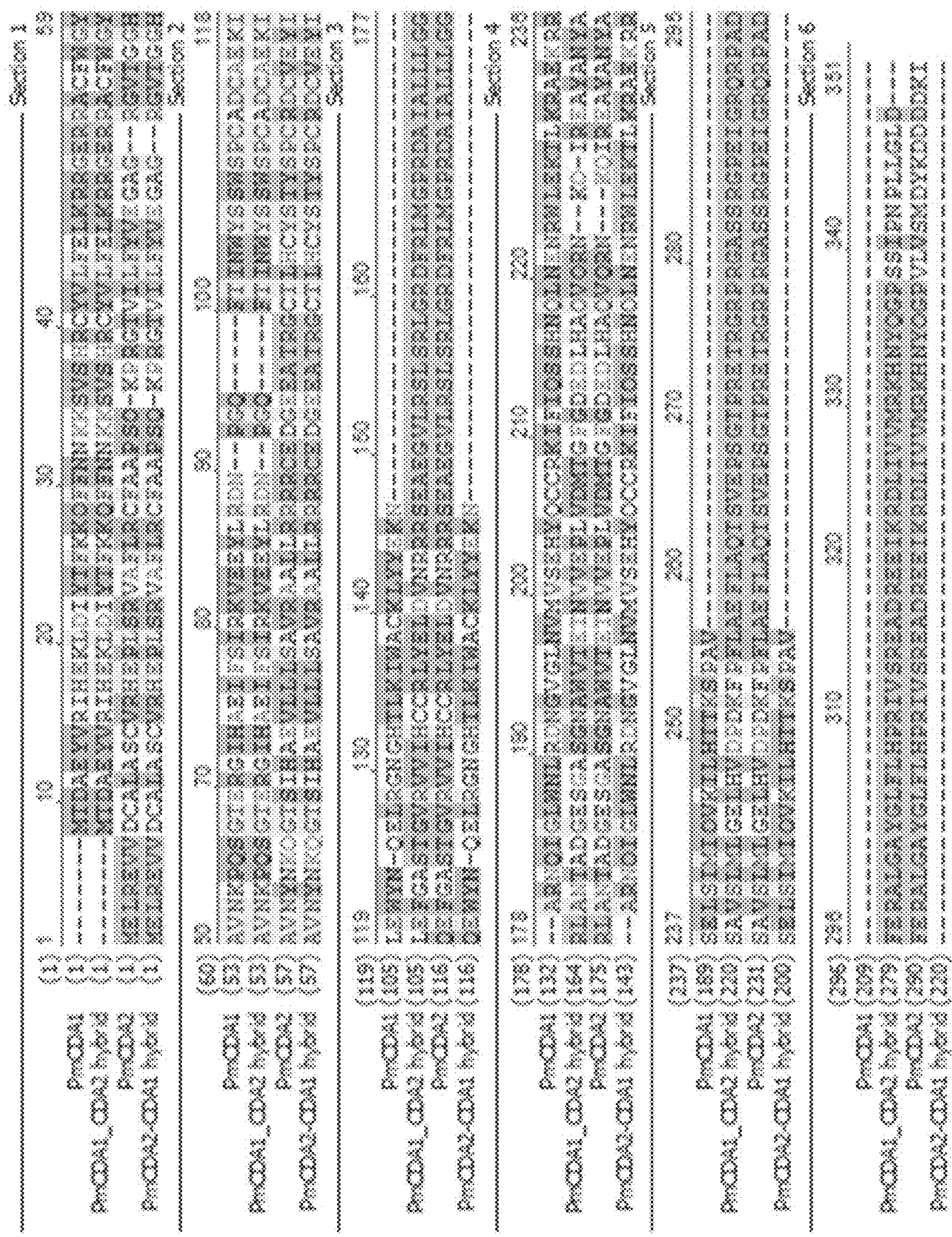
FIG. 3C shows a sequence alignment of sea lamprey CDA1 (PmCDA1, SEQ ID NO:3) sea lamprey CDA2 (PmCDA2, SEQ ID NO:4), chimeras between the two CDA1 and CDA2 (SEQ ID NO:5 and SEQ ID NO:6).
Figure 4B:
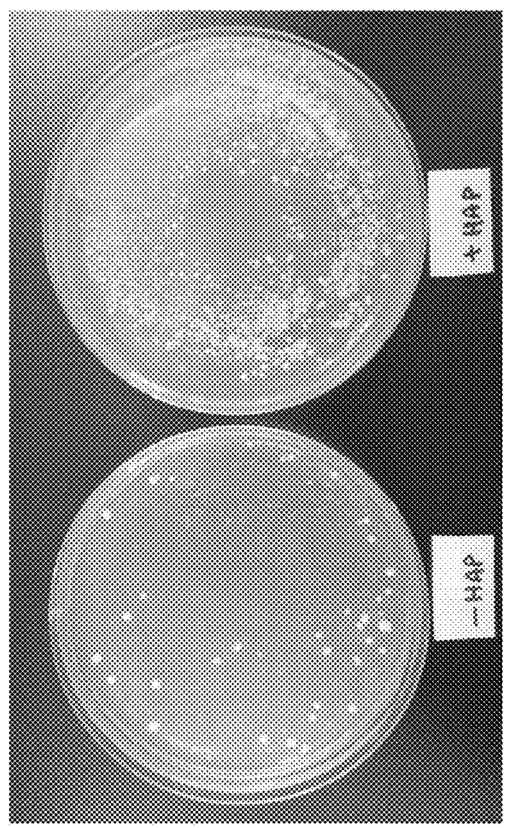
FIGS. 4A, 4B and 4C show hypermutation patch tests (FIG. 4A and FIG. 4C) and spot test (FIG. 4B) of forward mutations in the yeast CAN1 gene induced by overexpression of full length cytosine deaminase PmCDA1 (FIG. 4A), various variants of PmCDA1 and PmCDA2 (FIG. 4C) and exposure to the replication fidelity compromising compound HAP (FIG. 4B). Left sides—no inducers are present; Right side—yeast are exposed to inducers.
Figure 4A:
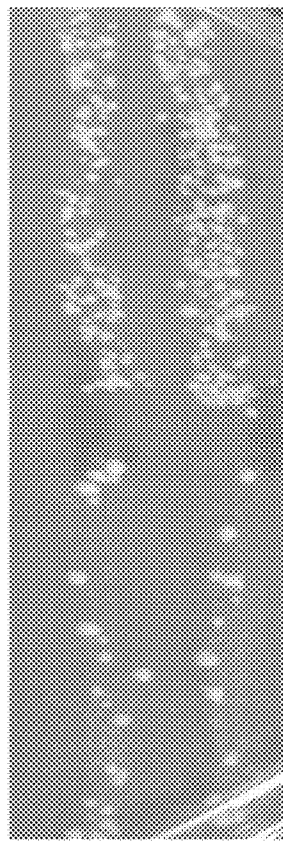
Figure 4C:
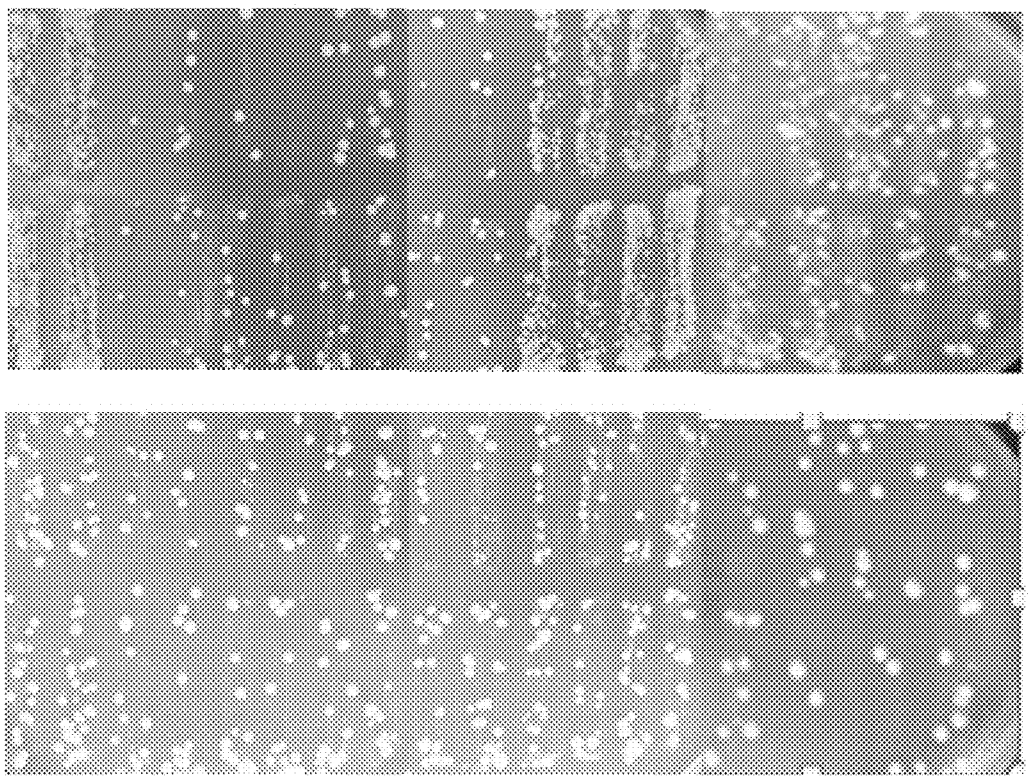
Figure 5:
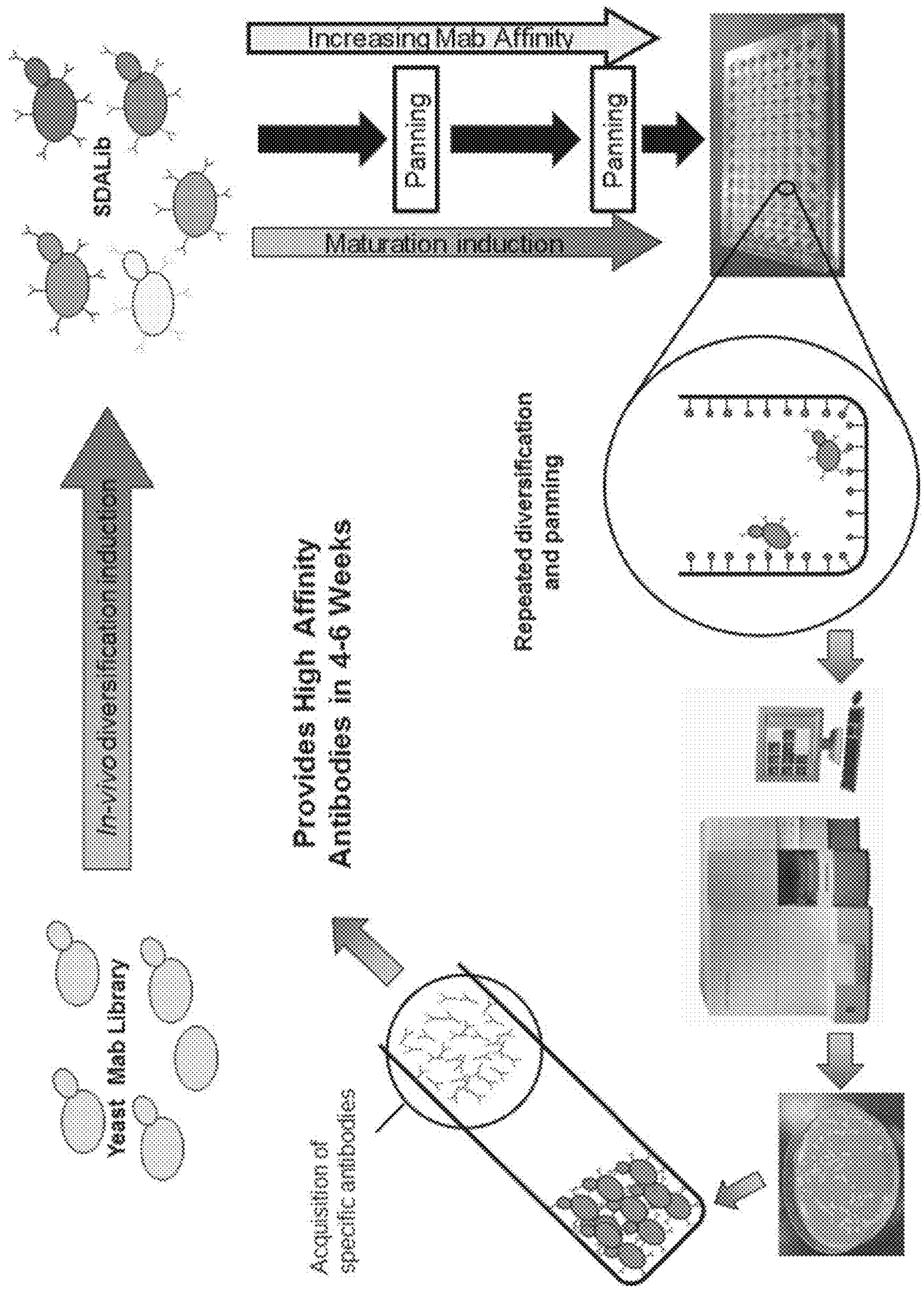
FIG. 5 is a schematic diagram of the antibody discovery system of the present invention.
Figure 7A:
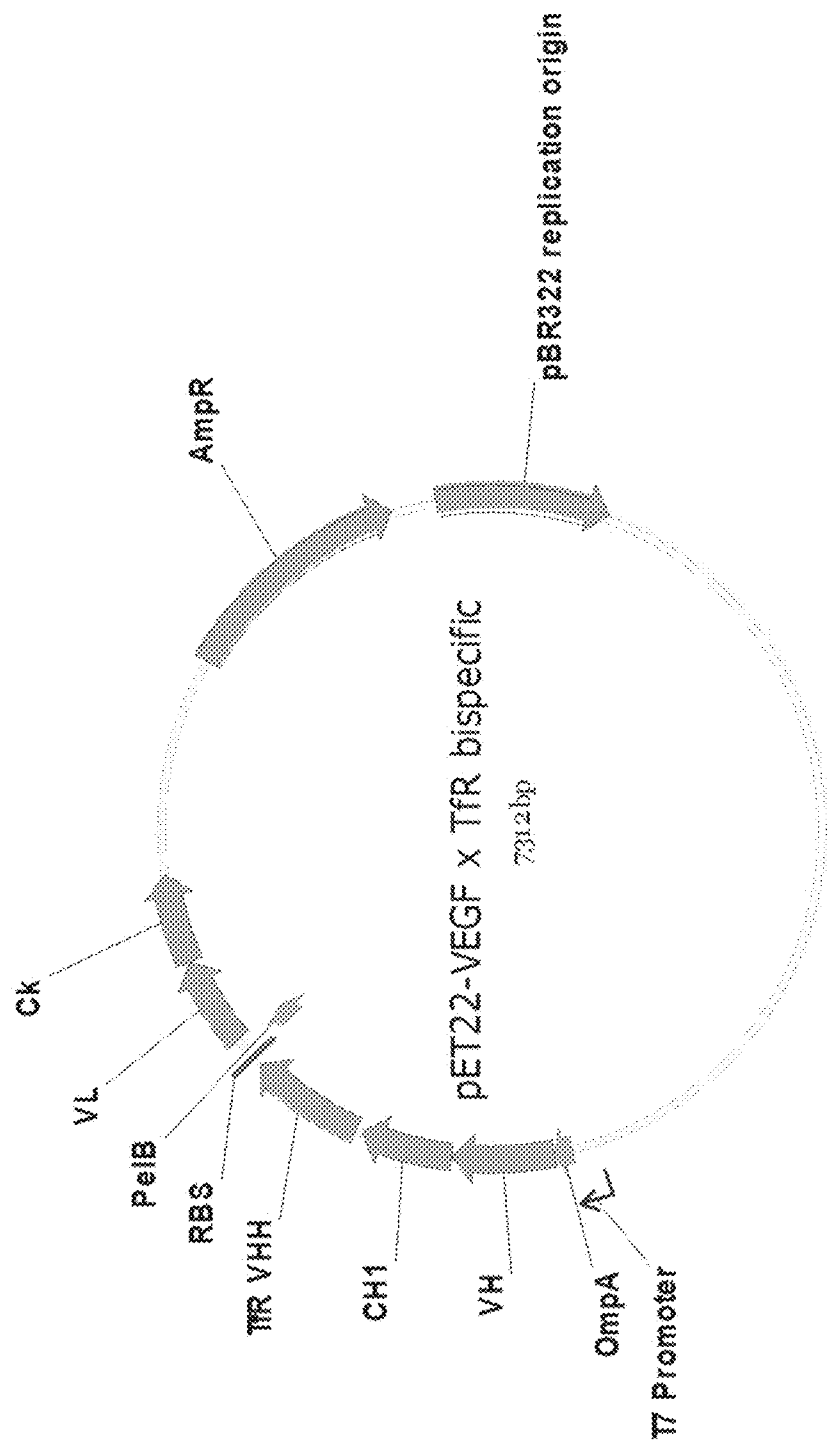
FIGS. 7A and 7B present vectors for expressing bispecific functional agents.
Figure 7B:
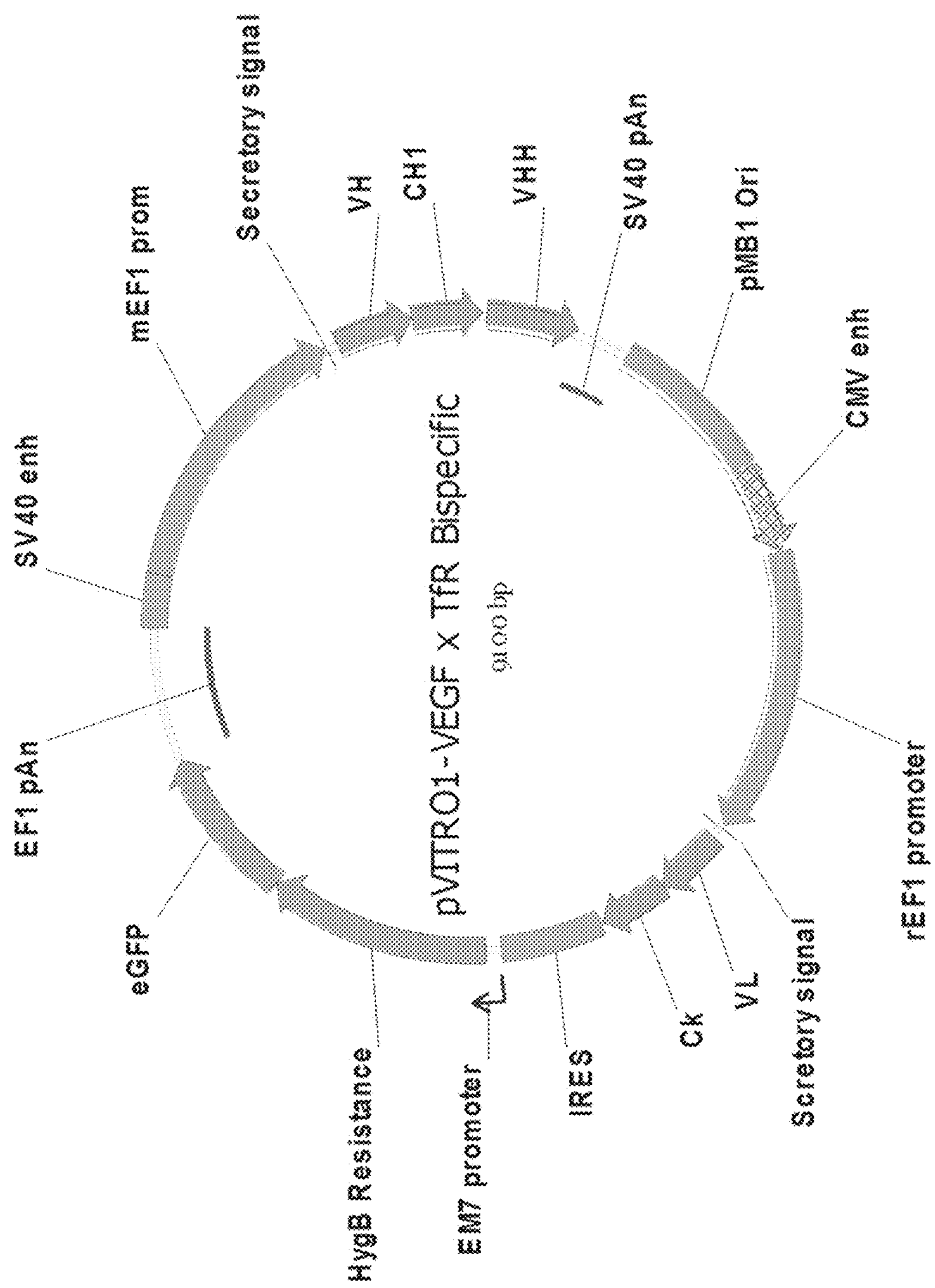
Figure 8:
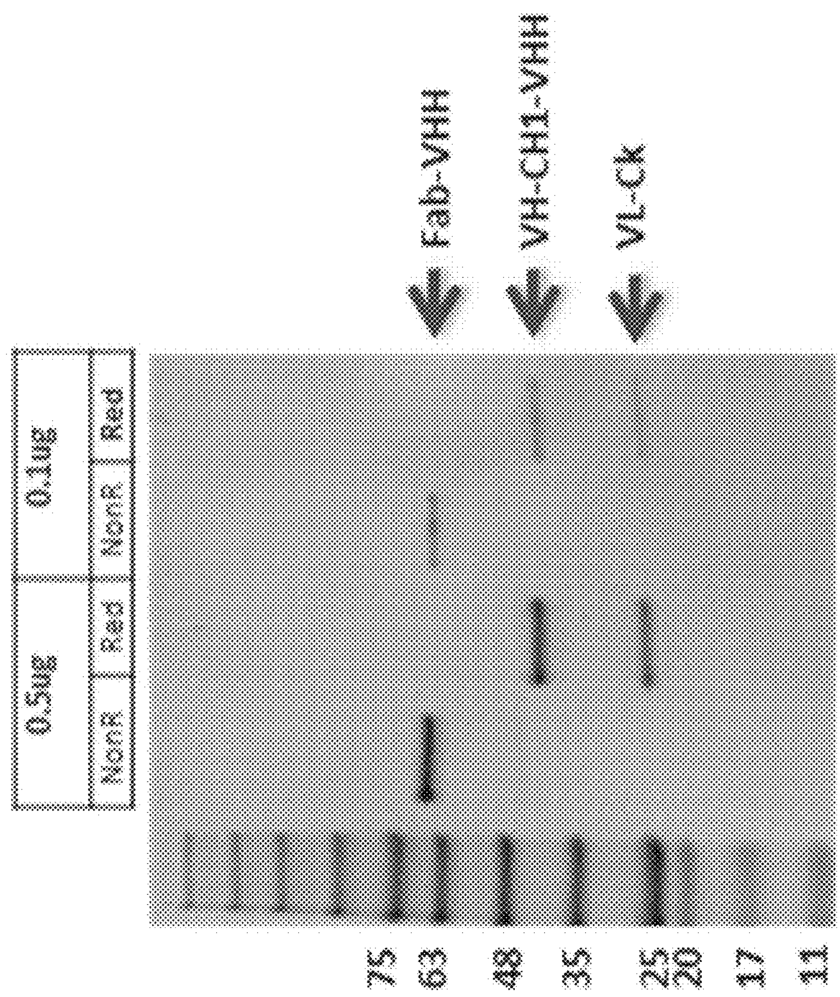
FIG. 8 shows an SDS-PAGE gel showing VEGF×TfR bispecific antibody expressed and purified from a mammalian system. Lane 1—protein ladder; Lane 2 and lane 4—not reduced, Lane 3 and lane 5—reduced.
Figure 9:
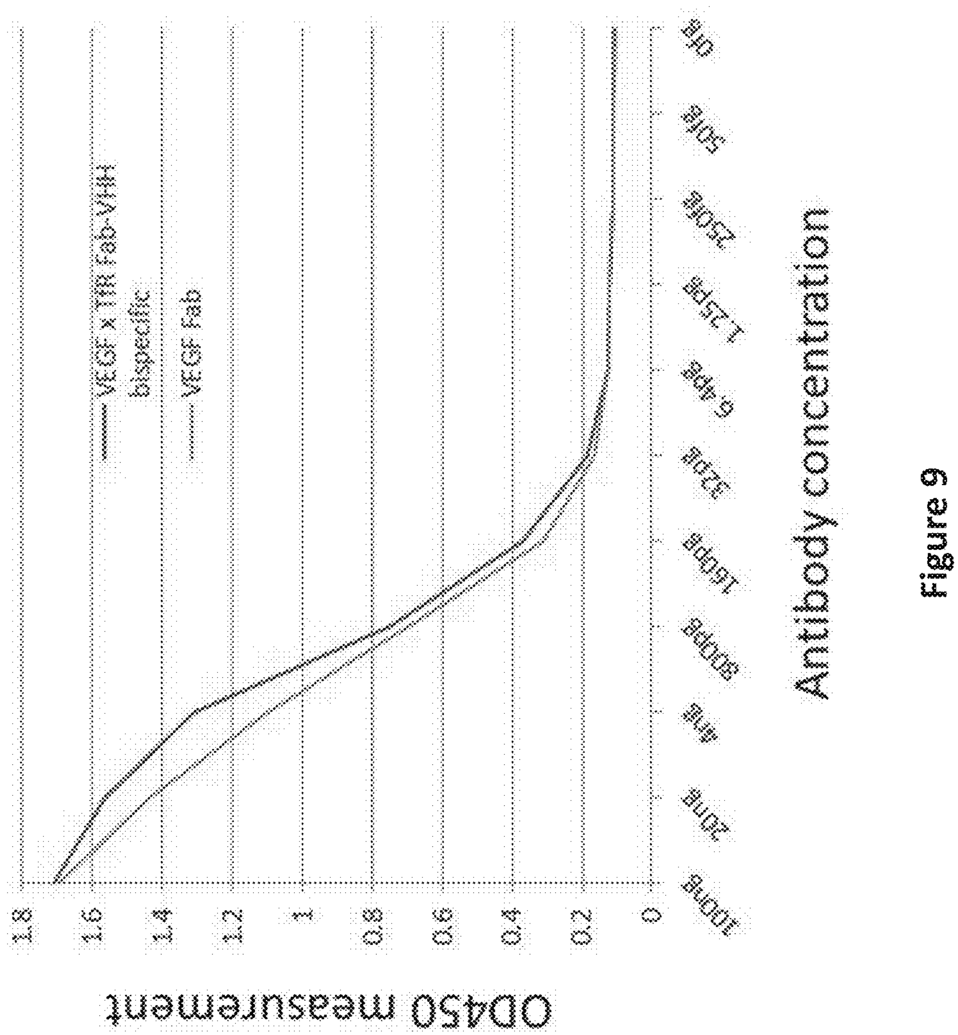
FIG. 9 shows ELISA assay where coated VEGF165 recombinant protein was probed with VEGF×TfR bispecific and VEGF monospecific antibodies. ELISA plate was coated with human VEGF165 protein at 0.1 ug/well. Various antibody concentrations were added. Bound antibodies were detected using goat anti-human IgG Fab HRP and TMB substrate. The data show that the binding activity of anti-VEGF Fab fragment to VEGF is similar in the monospecific and the bispecific format.
Figure 10:
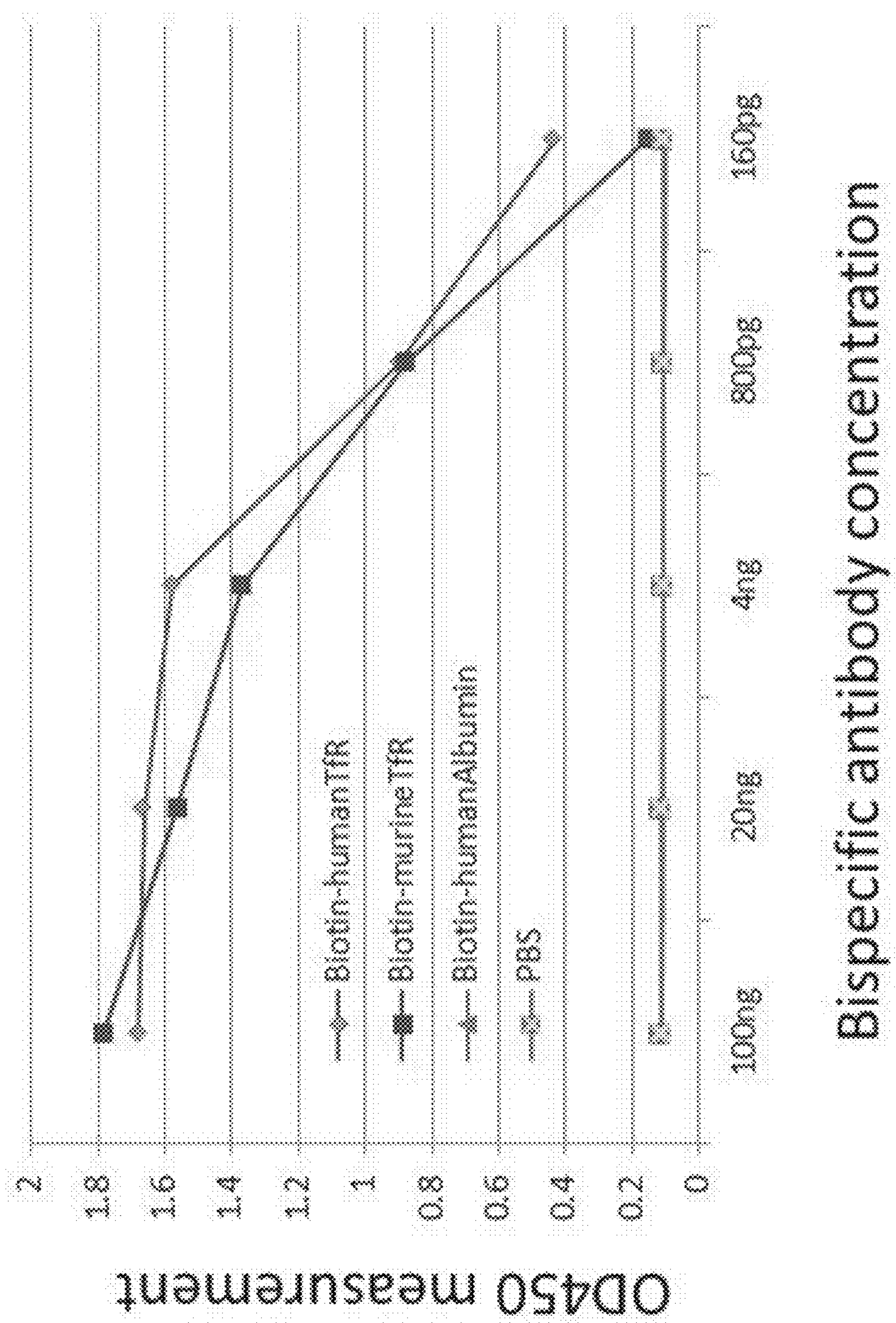
FIG. 10 shows bispecific ELISA where ELISA plate was coated with human VEGF165 protein at 0.1 ug/well. Various VEGF×TfR antibody amounts were added followed by adding biotinylated human TfR or murine TfR or biotinylated human albumin (0.1 ug/well) or PBS. Bound biotinylated proteins were detected by streptavidin-HRP. The data show that VEGF×TfR binds both human and murine TfRs with similar affinity. No binding to biotinylated human albumin is observed.

The protein sequences provided herewith are as follows:

| | |
|---|---|
| SEQ ID NO: 1 | An exemplary linker sequence that can be used to join the polypeptide binder with the modular scaffold |
| SEQ ID NO: 2 | An exemplary linker sequence that can be used to join the polypeptide binder with the modular scaffold |
| SEQ ID NO: 3 | Sea lamprey CDA1 |
| SEQ ID NO: 4 | Sea lamprey CDA2 |
| SEQ ID NO: 5 | Chimeric sea lamprey CDA1-CDA2 hybrid |
| SEQ ID NO: 6 | Chimeric sea lamprey CDA2-CDA1 hybrid |
| SEQ ID NO: 7 | AGA2 |
| SEQ ID NO: 8 | AGA1 |
| SEQ ID NO: 9 | Vector of FIG. 2 |
| SEQ ID NO: 10 | Vector of FIG. 3A |
| SEQ ID NO: 11 | Vector of FIG. 3B |
| SEQ ID NO: 12 | Vector of FIG. 7A |
| SEQ ID NO: 13 | Vector of FIG. 7B |

The invention further relates to the following numbered embodiments:

Embodiment A1. A method of producing a bispecific functional binding agent, wherein the bispecific functional binding agent comprises a polypeptide binder with a given target specificity fused at its C-terminus with a selected modular scaffold, wherein the selected modular scaffold binds to a distinct second target, wherein the method comprises the steps of: (a) providing a eukaryotic cell culture, (b) displaying, at the outer surface of the cells, a library of modular scaffolds fused at their N-terminus to prey polypeptide, (b) contacting said library with said antigen, (c) selecting a modular scaffold library member binding to the antigen, (d) recombinantly producing a resulting nucleic acid construct of an alpha nucleic acid expressing the selected modular scaffold fused to a beta nucleic acid expressing the peptide binder such that the construct expresses the bispecific functional binding agent, and (e) expressing the bispecific functional binding agent for the resulting nucleic acid construct.

Embodiment B1. A method for affinity maturing and identifying an antigen-binding variant of a modular scaffold comprising: A. cultivating a culture of eukaryotic cells comprising: a) recombinant DNA configured to express a mutagenic cytidine deaminase, b) second recombinant DNA configured to express a membrane-bound bait polypeptide, and c) third recombinant DNA configured to express the modular scaffold, with the modular scaffold operably fused to the C-terminus of a prey polypeptide, defining a fusion polypeptide, wherein the culture of cells in combination is configured to express a library of modular scaffolds in said fusion polypeptides; B. cultivating the culture such that the cytidine deaminase is expressed; C. optionally, contacting the culture with a mutagen—6-N hydroxyaminopurine; D. thereafter cultivating the culture such that the membrane-bound bait polypeptide and the library of modular scaffold fusion polypeptides are expressed; and E. selecting a subset of the eukaryotic cells that express modular scaffold protein at the cell surface that binds the antigen significantly stronger than the rest of the cells.

Embodiment A2. The method of an A Embodiment, wherein the eukaryotic cells of the culture comprise: a) recombinant DNA configured to express a mutagenic cytidine deaminase; b) second recombinant DNA configured to express a membrane-bound bait polypeptide; and c) third recombinant DNA configured to express a modular scaffold, with the modular scaffold operably fused to the C-terminus of a prey polypeptide.

Embodiment A3. The method of an A or B Embodiment, wherein the cytidine deaminase expressed by the first recombinant DNA is sea lamprey Petromyzon marinus cytidine deaminase CDA1 or functional fragment thereof.

Embodiment A4. The method of an A or B Embodiment, wherein the bait polypeptide expressed by the second recombinant DNA is whole *Saccharomyces cerevisiae* AGA1 or a functional fragment thereof, and comprises a cell surface anchor.

Embodiment A5. The method of Embodiment 4, wherein the cell surface anchor comprises a polypeptide segment sufficient to incorporate into the membrane, trigger a covalent association with lipid (e.g., GPI), or associate with another membrane component.

Embodiment A6. The method of an A or B Embodiment, wherein the prey polypeptide expressed by the third recombinant DNA comprises *Saccharomyces cerevisiae* AGA2 or a functional fragment thereof capable of forming a heterodimeric complex with the membrane-bound bait.

Embodiment A7. The method of an A or B Embodiment, wherein the scaffold protein expressed by the third recombinant DNA comprises an immunoglobulin heavy chain variable region, an immunoglobulin light chain variable region, Anticalins, Fibronectin type III domain, Designed Ankyrin Repeat Protein or Centyrin.

Embodiment A8. The method of an A or B Embodiment, wherein the cell provided is a *Saccharomyces* cell or *Pichia* cell.

Embodiment A9. The method of an A or B Embodiment, wherein the cell provided is a Chinese hamster ovary cell.

Embodiment A10. The method of an A or B Embodiment, wherein the modular scaffold is a single stranded polypeptide.

Embodiment A12. The method of an A Embodiment, wherein the expressed bispecific functional binding agent comprises, oriented from N-terminal to C-terminal: A. A polypeptide binder; B. A linker; and C. A selected modular scaffold.

Embodiment A13. The method of an A or B Embodiment, wherein in the expressed bispecific functional binding agent comprises a linker that comprises an amino acid sequence of SEQ ID 1 or SEQ ID 2.

Embodiment A14. A modular scaffold selected for binding affinity pursuant to an A or B Embodiment.

Embodiment A15. A bispecific functional binding agent comprising a sequence comprising, from N-terminal to C-terminal, a polypeptide binder or subunit thereof and a ligand-binding scaffold protein, wherein the modular scaffold is selected for binding affinity pursuant to an A or B Embodiment.

Embodiment C1. A method of producing a bispecific functional binding agent, wherein the bispecific functional binding agent comprises a polypeptide binder with a given target specificity fused at its C-terminus with a selected modular scaffold, wherein the selected modular scaffold binds to a distinct second target, wherein the method comprises the steps of: (a) displaying, at the outer surface of cells of a eukaryotic cell culture, a library of modular scaffolds fused at their N-terminus to prey polypeptide; (b) contacting said library with said antigen; (c) selecting a modular scaffold library member binding to the antigen, the member comprising one of the eukaryotic cells expressing an alpha nucleic acid encoding a corresponding modular scaffold; (d) recombinantly producing a resulting nucleic acid construct of the alpha nucleic acid fused to a beta nucleic acid expressing the peptide binder such that the construct expresses the bispecific functional binding agent; and (e) expressing the bispecific functional binding agent for the resulting nucleic acid construct.

Embodiment D2. A method for affinity maturing and identifying an antigen-binding variant of a modular scaffold comprising: A. cultivating a culture of eukaryotic cells comprising: a) recombinant DNA configured to express a mutagenic cytidine deaminase, b) second recombinant DNA configured to express a membrane-bound bait polypeptide, and c) a library of third recombinant DNAs configured to express the modular scaffold, with the modular scaffold operably fused to the C-terminus of a prey polypeptide, defining a fusion polypeptide, wherein the culture of cells in combination is configured to express the library of modular scaffolds in said fusion polypeptides; B. cultivating the culture such that the cytidine deaminase is expressed; C. thereafter cultivating the culture such that the membrane-bound bait polypeptide and the library of modular scaffold fusion polypeptides are expressed; and D. selecting a subset of the eukaryotic cells that express modular scaffold protein at the cell surface that binds the antigen significantly stronger than the rest of the cells.

Embodiment C2. The method of an A, B, C or D embodiment, wherein the eukaryotic cells of the culture comprise: 1) recombinant DNA configured to express a mutagenic cytidine deaminase; 2) second recombinant DNA configured to express a membrane-bound bait polypeptide; and 3) third recombinant DNA configured to express a modular scaffold, with the modular scaffold operably fused to the C-terminus of a prey polypeptide.

Embodiment C3. The method of an A, B, C or D embodiment, wherein the cytidine deaminase expressed by the first recombinant DNA is sea lamprey Petromyzon marinus cytidine deaminase CDA1 or a functional fragment thereof.

Embodiment C4. The method of an A, B, C or D embodiment, wherein the bait polypeptide expressed by the second recombinant DNA is whole *Saccharomyces cerevisiae* AGA1 or a functional fragment thereof, and comprises a cell surface anchor.

Embodiment C5. The method of an A, B, C or D embodiment, wherein the cell surface anchor comprises a polypeptide segment sufficient to incorporate into the membrane, trigger a covalent association with lipid (e.g., GPI), or associate with another membrane component.

Embodiment C6. The method of an A, B, C or D embodiment, wherein the prey polypeptide expressed by the third recombinant DNA comprises *Saccharomyces cerevisiae* AGA2 or a functional fragment thereof capable of forming a heterodimeric complex with the membrane-bound bait.

Embodiment C7. The method of an A, B, C or D embodiment, wherein the scaffold protein expressed by the third recombinant DNA comprises an immunoglobulin heavy chain variable region, an immunoglobulin light chain variable region, Anticalins, Fibronectin type III domain, Designed Ankyrin Repeat Protein or Centyrin.

Embodiment C8. The method of an A, B, C or D embodiment, wherein the cell provided is a *Saccharomyces* cell or *Pichia* cell.

Embodiment C9. The method of an A, B, C or D embodiment, wherein the cell provided is a Chinese hamster ovary cell.

Embodiment C10. The method of an A, B, C or D embodiment, comprising as elements of the selecting step: (c1) expressing the second recombinant DNA and selecting the modular scaffold library member via membrane bound molecular scaffold; (c2) expressing in a cell line derived from the selected cell a fourth recombinant DNA configured to express a soluble-bound bait polypeptide; and (c3) confirming antigen binding with a soluble molecular scaffold derived from the cell line.

Embodiment C11. The method of an A, B, C or D embodiment, wherein the modular scaffold is a single stranded polypeptide.

Embodiment C12. The method of an A, B, C or D embodiment, wherein the expressed binding agent comprises, oriented from N-terminal to C-terminal: A. A polypeptide binder; B. A linker; and C. A selected modular scaffold.

Embodiment C13. The method of an A, B, C or D embodiment, wherein in the expressed binding agent the polypeptide binder comprises an immunoglobulin heavy chain variable region, a light chain variable region, combinations of light and heavy chain regions, Anticalins, Fibronectin type III domain, Designed Ankyrin Repeat Protein or Centyrin.

Embodiment C14. The method of an A, B, C or D embodiment, wherein in the expressed bispecific functional binding agent the linker comprises an amino acid sequence of SEQ ID 1 or SEQ ID 2.

Embodiment C17. The method of an A, B, C or D embodiment, further comprising: contacting the culture with a mutagen while cytidine deaminase is expressed.

Embodiment C18. The method of Embodiment C17, wherein the mutagen is 6-N hydroxyaminopurine.

Embodiment E1. A binding agent comprising a sequence comprising, from N-terminal to C-terminal, a polypeptide binder or subunit thereof and a ligand-binding scaffold protein, wherein a sequence for the modular scaffold is selected for binding affinity pursuant to an A, B, C or D embodiment.

Embodiment E2. A binding agent constructed pursuant to an A, B, C or D embodiment.

CITATIONS

ATWELL, S., J. B. RIDGWAY, J. A. WELLS and P. CARTER, 1997 Stable heterodimers from remodeling the domain interface of a homodimer using a phage display library. J Mol Biol 270: 26-35.

BARGOU, R., E. LEO, G. ZUGMAIER, M. KLINGER, M. GOEBELER et al., 2008 Tumor regression in cancer patients by very low doses of a T cell-engaging antibody. Science 321: 974-977.

BEERLI, R. R., M. BAUER, R. B. BUSER, M. GWERDER, S. MUNTWILER et al., 2008 Isolation of human monoclonal antibodies by mammalian cell display. Proc Natl Acad Sci USA 105: 14336-14341.

BODER, E. T., and K. D. WITTRUP, 1997 Yeast surface display for screening combinatorial polypeptide libraries. Nat Biotechnol 15: 553-557.

BODER, E. T., and K. D. WITTRUP, 2000 Yeast surface display for directed evolution of protein expression, affinity, and stability. Methods Enzymol 328: 430-444.

BOSTROM, J., S. F. YU, D. KAN, B. A. APPLETON, C. V. LEE et al., 2009 Variants of the antibody herceptin that interact with HER2 and VEGF at the antigen binding site. Science 323: 1610-1614.

CHAO, G., W. L. LAU, B. J. HACKEL, S. L. SAZINSKY, S. M. LIPPOW et al., 2006 Isolating and engineering human antibodies using yeast surface display. Nat Protoc 1: 755-768.

CHOI, B. D., M. CAI, D. D. BIGNER, A. I. MEHTA, C. T. KUAN et al., 2011 Bispecific antibodies engage T cells for antitumor immunotherapy. Expert Opin Biol Ther 11: 843-853.

CONRATH, K. E., M. LAUWEREYS, M. GALLENI, A. MATAGNE, J. M. FRERE et al., 2001 Beta-lactamase inhibitors derived from single-domain antibody fragments elicited in the camelidae. Antimicrob Agents Chemother 45: 2807-2812.

DAVIS, J. H., C. APERLO, Y. LI, E. KUROSAWA, Y. LAN et al., 2010 SEEDbodies: fusion proteins based on strand-exchange engineered domain (SEED) CH3 heterodimers in an Fc analogue platform for asymmetric binders or immunofusions and bispecific antibodies. Protein Eng Des Sel 23: 195-202.

DOPPALAPUDI, V. R., J. HUANG, D. LIU, P. JIN, B. LIU et al., 2010 Chemical generation of bispecific antibodies. Proc Natl Acad Sci USA 107: 22611-22616.

DRAKE, J. W., B. CHARLESWORTH, D. CHARLESWORTH and J. F. CROW, 1998 Rates of spontaneous mutation. Genetics 148: 1667-1686.

DUNCAN, B. K., and J. H. MILLER, 1980 Mutagenic deamination of cytosine residues in DNA. Nature 287: 560-561.

ECKER, D. M., S. D. JONES and H. L. LEVINE, 2015 The therapeutic monoclonal antibody market. MAbs 7: 9-14.

FENG, M., W. GAO, R. WANG, W. CHEN, Y. G. MAN et al., 2013 Therapeutically targeting glypican-3 via a conformation-specific single-domain antibody in hepatocellular carcinoma. Proc Natl Acad Sci USA 110: E1083-1091.

GREENBERG, A. S., D. AVILA, M. HUGHES, A. HUGHES, E. C. MCKINNEY et al., 1995 A new antigen receptor gene family that undergoes rearrangement and extensive somatic diversification in sharks. Nature 374: 168-173.

GUNASEKARAN, K., M. PENTONY, M. SHEN, L. GARRETT, C. FORTE et al., 2010 Enhancing antibody Fc heterodimer formation through electrostatic steering effects: applications to bispecific molecules and monovalent IgG. J Biol Chem 285: 19637-19646.

HAMERS-CASTERMAN, C., T. ATARHOUCH, S. MUYLDERMANS, G. ROBINSON, C. HAMERS et al., 1993 Naturally occurring antibodies devoid of light chains. Nature 363: 446-448.

HANES, J., and A. PLUCKTHUN, 1997 In vitro selection and evolution of functional proteins by using ribosome display. Proc Natl Acad Sci USA 94: 4937-4942.

HAWKINS, R. E., S. J. RUSSELL and G. WINTER, 1992 Selection of phage antibodies by binding affinity. Mimicking affinity maturation. J Mol Biol 226: 889-896.

HE, M., and M. J. TAUSSIG, 1997 Antibody-ribosome-mRNA (ARM) complexes as efficient selection particles for in vitro display and evolution of antibody combining sites. Nucleic Acids Res 25: 5132-5134.

HUSTON, J. S., D. LEVINSON, M. MUDGETT-HUNTER, M. S. TAI, J. NOVOTNY et al., 1988 Protein engineering of antibody binding sites: recovery of specific activity in an anti-digoxin single-chain Fv analogue produced in *Escherichia coli*. Proc Natl Acad Sci USA 85: 5879-5883.

JUNG, G., U. FREIMANN, Z. VON MARSCHALL, R. A. REISFELD and W. WILMANNS, 1991 Target cell-induced T cell activation with bi- and trispecific antibody fragments. Eur J Immunol 21: 2431-2435.

KRAEBER-BODERE, F., C. BODET-MILIN, C. ROUSSEAU, T. EUGENE, A. PALLARDY et al., 2014 Radioimmunoconjugates for the treatment of cancer. Semin Oncol 41: 613-622.

LANG, G. I., and A. W. MURRAY, 2008 Estimating the per-base-pair mutation rate in the yeast *Saccharomyces cerevisiae*. Genetics 178: 67-82.

MACK, M., G. RIETHMULLER and P. KUFER, 1995 A small bispecific antibody construct expressed as a functional single-chain molecule with high tumor cell cytotoxicity. Proc Natl Acad Sci USA 92: 7021-7025.

MAYOROV, V. I., I. B. ROGOZIN, L. R. ADKISON, C. FRAHM, T. A. KUNKEL et al., 2005a Expression of human AID in yeast induces mutations in context similar to the context of somatic hypermutation at G-C pairs in immunoglobulin genes. BMC Immunol 6: 10.

MAYOROV, V. I., I. B. ROGOZIN, L. R. ADKISON, C. FRAHM, T. A. KUNKEL et al., 2005b Expression of human AID in yeast induces mutations in context similar to the context of somatic hypermutation at G-C pairs in immunoglobulin genes. BMC Immunol 6: 10.

MERCHANT, A. M., Z. ZHU, J. Q. YUAN, A. GODDARD, C. W. ADAMS et al., 1998 An efficient route to human bispecific IgG. Nat Biotechnol 16: 677-681.

NOSKOV, V. N., K. STAAK, P. V. SHCHERBAKOVA, S. G. KOZMIN, K. NEGISHI et al., 1996 HAM1, the gene controlling 6-N-hydroxylaminopurine sensitivity and mutagenesis in the yeast *Saccharomyces cerevisiae*. Yeast 12: 17-29.

PACK, P., and A. PLUCKTHUN, 1992 Miniantibodies: use of amphipathic helices to produce functional, flexibly linked dimeric FV fragments with high avidity in *Escherichia coli*. Biochemistry 31: 1579-1584.

PANTEL, K., G. SCHLIMOK, D. KUTTER, G. SCHALLER, T. GENZ et al., 1991 Frequent down-regulation of major histocompatibility class I antigen expression on individual micrometastatic carcinoma cells. Cancer Res 51: 4712-4715.

PEREZ, P., R. W. HOFFMAN, S. SHAW, J. A. BLUESTONE and D. M. SEGAL, 1985 Specific targeting of cytotoxic T cells by anti-T3 linked to anti-target cell antibody. Nature 316: 354-356.

REIERSEN, H., I. LOBERSLI, G. A. LOSET, E. HVATTUM, B. SIMONSEN et al., 2005 Covalent antibody display—an in vitro antibody-DNA library selection system. Nucleic Acids Res 33: e10.

RIDGWAY, J. B., L. G. PRESTA and P. CARTER, 1996 'Knobs-into-holes' engineering of antibody CH3 domains for heavy chain heterodimerization. Protein Eng 9: 617-621.

ROGOZIN, I. B., L. M. IYER, L. LIANG, G. V. GLAZKO, V. G. LISTON et al., 2007 Evolution and diversification of lamprey antigen receptors: evidence for involvement of an AID-APOBEC family cytosine deaminase. Nat Immunol 8: 647-656.

ROSSI, E. A., D. M. GOLDENBERG, T. M. CARDILLO, W. J. MCBRIDE, R. M. SHARKEY et al., 2006 Stably tethered multifunctional structures of defined composition made by the dock and lock method for use in cancer targeting. Proc Natl Acad Sci USA 103: 6841-6846.

SAPPARAPU, G., S. A. PLANQUE, Y. NISHIYAMA, S. K. FOUNG and S. PAUL, 2009 Antigen-specific proteolysis by hybrid antibodies containing promiscuous proteolytic light chains paired with an antigen-binding heavy chain. J Biol Chem 284: 24622-24633.

SCHAEFER, W., J. T. REGULA, M. BANNER, J. SCHANZER, R. CROASDALE et al., 2011 Immunoglobulin domain crossover as a generic approach for the production of bispecific IgG antibodies. Proc Natl Acad Sci USA 108: 11187-11192.

SHCHERBAKOVA, P. V., and Y. I. PAVLOV, 1993 Mutagenic specificity of the base analog 6-N-hydroxylaminopurine in the URA3 gene of the yeast *Saccharomyces cerevisiae.* Mutagenesis 8: 417-421.

SIKORSKI, R. S., and P. HIETER, 1989 A system of shuttle vectors and yeast host strains designed for efficient manipulation of DNA in *Saccharomyces cerevisiae.* Genetics 122: 19-27.

STAERZ, U. D., O. KANAGAWA and M. J. BEVAN, 1985 Hybrid antibodies can target sites for attack by T cells. Nature 314: 628-631.

STUDIER, F. W., 2005 Protein production by auto-induction in high density shaking cultures. Protein Expr Purif 41: 207-234.

VU, K. B., M. A. GHAHROUDI, L. WYNS and S. MUYLDERMANS, 1997 Comparison of llama VH sequences from conventional and heavy chain antibodies. Mol Immunol 34: 1121-1131.

WARD, E. S., D. GUSSOW, A. D. GRIFFITHS, P. T. JONES and G. WINTER, 1989 Binding activities of a repertoire of single immunoglobulin variable domains secreted from *Escherichia coli.* Nature 341: 544-546.

WEIR, M., and J. B. KEENEY, 2014 PCR mutagenesis and gap repair in yeast. Methods Mol Biol 1205: 29-35.

Publications and references, including but not limited to patents and patent applications, cited in this specification are herein incorporated by reference in their entirety in the entire portion cited as if each individual publication or reference were specifically and individually indicated to be incorporated by reference herein as being fully set forth. Any patent application to which this application claims priority is also incorporated by reference herein in the manner described above for publications and references.

What is claimed:

1. A method of producing a bispecific functional binding agent, wherein the bispecific functional binding agent comprises a polypeptide binder with a given target specificity fused at its C-terminus with a selected modular scaffold, wherein the selected modular scaffold binds to a distinct second target, wherein the method comprises the steps of:

(a) displaying, at the outer surface of cells of a eukaryotic cell culture, a library of modular scaffolds fused at their N-terminus to prey polypeptide, (b) contacting said library with an antigen that is the second target, (c) selecting a modular scaffold library member binding to the antigen, the member comprising one of the eukaryotic cells expressing an alpha nucleic add encoding a corresponding modular scaffold, (d) recombinantly producing a resulting nucleic add construct of the alpha nucleic add fused to a beta nucleic acid expressing the polypeptide binder such that the construct expresses the bispecific functional binding agent, and (e) expressing the bispecific functional binding agent for the resulting nucleic acid construct.

2. The method of claim 1, wherein the eukaryotic cells of the culture comprise:

1) recombinant DNA configured to express a mutagenic cytidine deaminase;

2) second recombinant DNA configured to express a membrane-bound bait polypeptide; and 3) third recombinant DNA configured to express a modular scaffold, with the modular scaffold operably fused to the C-terminus of a prey polypeptide.

3. The method of claim 2, wherein the cytidine deaminase expressed by the first recombinant DNA is sea lamprey Petromyzon marinus cytidine deaminase CDA1 or a functional fragment thereof.

4. The method of claim 2, wherein the bait polypeptide expressed by the second recombinant DNA is whole *Saccharomyces cerevisiae* AGA1 or a functional fragment thereof, and comprises a cell surface anchor.

5. The method of claim 4, wherein the cell surface anchor comprises a polypeptide segment sufficient to incorporate into the membrane, trigger a covalent association with lipid (e.g., GPI), or associate with another membrane component.

6. The method of claim 2, wherein the prey polypeptide expressed by the third recombinant DNA comprises *Saccharomyces cerevisiae* AGA2 or a functional fragment thereof capable of forming a heterodimeric complex with the membrane-bound bait.

7. The method of claim 2, wherein the scaffold protein expressed by the third recombinant DNA comprises an immunoglobulin heavy chain variable region, an immunoglobulin light chain variable region, Anticalins, Fibronectin type III domain, Designed Ankyrin Repeat Protein or Centyrin.

8. The method of claim 2, wherein the cell provided is a *Saccharomyces* cell or *Pichia* cell.

9. The method of claim 2, wherein the cell provided is a Chinese hamster ovary cell.

10. The method of claim 2, comprising as elements of the selecting step:

(c1) expressing the second recombinant DNA and selecting the modular scaffold library member via membrane bound molecular scaffold;

(c2) expressing in a cell line derived from the selected cell a fourth recombinant DNA configured to express a soluble-bound bait polypeptide; and (c3) confirming antigen binding with a soluble molecular scaffold derived from the cell line.

11. The method of claim 1, wherein the modular scaffold is a single stranded polypeptide.

12. The method of claim 1, wherein the expressed bispecific functional binding agent comprises, oriented from N-terminal to C-terminal:

A. A polypeptide binder;

B. A linker; and

C. A selected modular scaffold.

13. The method of claim 12, wherein in the expressed bispecific functional binding agent the polypeptide binder comprises an immunoglobulin heavy chain variable region, a light chain variable region, combinations of light and heavy chain regions, Anticalins, Fibronectin type Ill domain, Designed Ankyrin Repeat Protein or Centyrin.

14. The method of claim 12, wherein in the expressed bispecific functional binding agent the linker comprises an amino acid sequence of SEQ ID 1 or SEQ ID 2.

15. A method for affinity maturing and identifying an antigen-binding variant of a modular scaffold comprising:

A. cultivating a culture of eukaryotic cells comprising:

a) recombinant DNA configured to express a mutagenic cytidine deaminase, b) second recombinant DNA configured to express a membrane-bound bait polypeptide, and c) a library of third recombinant DNAs configured to express the modular scaffold, with the modular scaffold operably fused to the C-terminus of a prey polypeptide, defining a fusion polypeptide, wherein the culture of cells in combination is configured to express the library of modular scaffolds in said fusion polypeptides;

B. cultivating the culture such that the cytidine deaminase is expressed;

C. thereafter cultivating the culture such that the membrane-bound bait polypeptide and the library of modular scaffold fusion polypeptides are expressed; and D. selecting a subset of the eukaryotic cells that express modular scaffold protein at the cell surface that binds the antigen significantly stronger than the rest of the cells.

16. The method of claim 15, further comprising:

B1. contacting the culture with a mutagen while cytidine deaminase is expressed.

17. The method of claim 16, wherein the mutagen is 6-N hydroxyaminopurine.

* * * * *

SEQUENCE LISTING

```
<160> NUMBER OF SEQ ID NOS: 13

<210> SEQ ID NO 1
<211> LENGTH: 11
<212> TYPE: PRT
<213> ORGANISM: Artificial Sequence
<220> FEATURE:
<223> OTHER INFORMATION: Synthetic linker

<400> SEQUENCE: 1

Arg Gly Arg Gly Arg Gly Arg Gly Gly Gly Arg
1               5                   10


<210> SEQ ID NO 2
<211> LENGTH: 16
<212> TYPE: PRT
<213> ORGANISM: Artificial Sequence
<220> FEATURE:
<223> OTHER INFORMATION: Synthetic linker

<400> SEQUENCE: 2

Gly Gly Gly Gly Gly Ser Gly Gly Gly Gly Ser Gly Gly Gly Gly Ser
1               5                   10                  15


<210> SEQ ID NO 3
<211> LENGTH: 208
<212> TYPE: PRT
<213> ORGANISM: Petromyzon marinus

<400> SEQUENCE: 3

Met Thr Asp Ala Glu Tyr Val Arg Ile His Glu Lys Leu Asp Ile Tyr
1               5                   10                  15
```

```
Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Trp Tyr Asn Gln Glu Leu
            100                 105                 110

Arg Gly Asn Gly His Thr Leu Lys Ile Trp Ala Cys Lys Leu Tyr Tyr
        115                 120                 125

Glu Lys Asn Ala Arg Asn Gln Ile Gly Leu Trp Asn Leu Arg Asp Asn
    130                 135                 140

Gly Val Gly Leu Asn Val Met Val Ser Glu His Tyr Gln Cys Cys Arg
145                 150                 155                 160

Lys Ile Phe Ile Gln Ser Ser His Asn Gln Leu Asn Glu Asn Arg Trp
                165                 170                 175

Leu Glu Lys Thr Leu Lys Arg Ala Glu Lys Arg Arg Ser Glu Leu Ser
            180                 185                 190

Ile Met Ile Gln Val Lys Ile Leu His Thr Thr Lys Ser Pro Ala Val
        195                 200                 205


<210> SEQ ID NO 4
<211> LENGTH: 345
<212> TYPE: PRT
<213> ORGANISM: Petromyzon marinus

<400> SEQUENCE: 4

Met Glu Leu Arg Glu Val Val Asp Cys Ala Leu Ala Ser Cys Val Arg
1               5                   10                  15

His Glu Pro Leu Ser Arg Val Ala Phe Leu Arg Cys Phe Ala Ala Pro
            20                  25                  30

Ser Gln Lys Pro Arg Gly Thr Val Ile Leu Phe Tyr Val Glu Gly Ala
        35                  40                  45

Gly Arg Gly Val Thr Gly Gly His Ala Val Asn Tyr Asn Lys Gln Gly
    50                  55                  60

Thr Ser Ile His Ala Glu Val Leu Leu Leu Ser Ala Val Arg Ala Ala
65                  70                  75                  80

Leu Leu Arg Arg Arg Arg Cys Glu Asp Gly Glu Glu Ala Thr Arg Gly
                85                  90                  95

Cys Thr Leu His Cys Tyr Ser Thr Tyr Ser Pro Cys Arg Asp Cys Val
            100                 105                 110

Glu Tyr Ile Gln Glu Phe Gly Ala Ser Thr Gly Val Arg Val Val Ile
        115                 120                 125

His Cys Cys Arg Leu Tyr Glu Leu Asp Val Asn Arg Arg Arg Ser Glu
    130                 135                 140

Ala Glu Gly Val Leu Arg Ser Leu Ser Arg Leu Gly Arg Asp Phe Arg
145                 150                 155                 160

Leu Met Gly Pro Arg Asp Ala Ile Ala Leu Leu Leu Gly Gly Arg Leu
                165                 170                 175

Ala Asn Thr Ala Asp Gly Glu Ser Gly Ala Ser Gly Asn Ala Trp Val
```

```
            180                 185                 190

Thr Glu Thr Asn Val Val Glu Pro Leu Val Asp Met Thr Gly Phe Gly
        195                 200                 205

Asp Glu Asp Leu His Ala Gln Val Gln Arg Asn Lys Gln Ile Arg Glu
    210                 215                 220

Ala Tyr Ala Asn Tyr Ala Ser Ala Val Ser Leu Met Leu Gly Glu Leu
225                 230                 235                 240

His Val Asp Pro Asp Lys Phe Pro Phe Leu Ala Glu Phe Leu Ala Gln
                245                 250                 255

Thr Ser Val Glu Pro Ser Gly Thr Pro Arg Glu Thr Arg Gly Arg Pro
            260                 265                 270

Arg Gly Ala Ser Ser Arg Gly Pro Glu Ile Gly Arg Gln Arg Pro Ala
        275                 280                 285

Asp Phe Glu Arg Ala Leu Gly Ala Tyr Gly Leu Phe Leu His Pro Arg
    290                 295                 300

Ile Val Ser Arg Glu Ala Asp Arg Glu Glu Ile Lys Arg Asp Leu Ile
305                 310                 315                 320

Val Val Met Arg Lys His Asn Tyr Gln Gly Pro Val Leu Val Ser Met
                325                 330                 335

Asp Tyr Lys Asp Asp Asp Asp Lys Ile
            340                 345


<210> SEQ ID NO 5
<211> LENGTH: 331
<212> TYPE: PRT
<213> ORGANISM: Artificial Sequence
<220> FEATURE:
<223> OTHER INFORMATION: Chimera derived from Petromyzon marinus

<400> SEQUENCE: 5

Met Thr Asp Ala Glu Tyr Val Arg Ile His Glu Lys Leu Asp Ile Tyr
1               5                   10                  15

Thr Phe Lys Lys Gln Phe Phe Asn Asn Lys Lys Ser Val Ser His Arg
            20                  25                  30

Cys Tyr Val Leu Phe Glu Leu Lys Arg Arg Gly Glu Arg Arg Ala Cys
        35                  40                  45

Phe Trp Gly Tyr Ala Val Asn Lys Pro Gln Ser Gly Thr Glu Arg Gly
    50                  55                  60

Ile His Ala Glu Ile Phe Ser Ile Arg Lys Val Glu Glu Tyr Leu Arg
65                  70                  75                  80

Asp Asn Pro Gly Gln Phe Thr Ile Asn Trp Tyr Ser Ser Trp Ser Pro
                85                  90                  95

Cys Ala Asp Cys Ala Glu Lys Ile Leu Glu Phe Gly Ala Ser Thr Gly
            100                 105                 110

Val Arg Val Val Ile His Cys Cys Arg Leu Tyr Glu Leu Asp Val Asn
        115                 120                 125

Arg Arg Arg Ser Glu Ala Glu Gly Val Leu Arg Ser Leu Ser Arg Leu
    130                 135                 140

Gly Arg Asp Phe Arg Leu Met Gly Pro Arg Asp Ala Ile Ala Leu Leu
145                 150                 155                 160

Leu Gly Gly Arg Leu Ala Asn Thr Ala Asp Gly Glu Ser Gly Ala Ser
                165                 170                 175

Gly Asn Ala Trp Val Thr Glu Thr Asn Val Val Glu Pro Leu Val Asp
            180                 185                 190

Met Thr Gly Phe Gly Asp Glu Asp Leu His Ala Gln Val Gln Arg Asn
```

```
        195                 200                 205

Lys Gln Ile Arg Glu Ala Tyr Ala Asn Tyr Ala Ser Ala Val Ser Leu
    210                 215                 220

Met Leu Gly Glu Leu His Val Asp Pro Asp Lys Phe Pro Phe Leu Ala
225                 230                 235                 240

Glu Phe Leu Ala Gln Thr Ser Val Glu Pro Ser Gly Thr Pro Arg Glu
                245                 250                 255

Thr Arg Gly Arg Pro Arg Gly Ala Ser Ser Arg Gly Pro Glu Ile Gly
            260                 265                 270

Arg Gln Arg Pro Ala Asp Phe Glu Arg Ala Leu Gly Ala Tyr Gly Leu
        275                 280                 285

Phe Leu His Pro Arg Ile Val Ser Arg Glu Ala Asp Arg Glu Glu Ile
    290                 295                 300

Lys Arg Asp Leu Ile Val Val Met Arg Lys His Asn Tyr Gln Gly Pro
305                 310                 315                 320

Ser Ser Ile Pro Asn Pro Leu Leu Gly Leu Asp
                325                 330


<210> SEQ ID NO 6
<211> LENGTH: 219
<212> TYPE: PRT
<213> ORGANISM: Artificial Sequence
<220> FEATURE:
<223> OTHER INFORMATION: Chimera derived from Petromyzon marinus

<400> SEQUENCE: 6

Met Glu Leu Arg Glu Val Val Asp Cys Ala Leu Ala Ser Cys Val Arg
1               5                   10                  15

His Glu Pro Leu Ser Arg Val Ala Phe Leu Arg Cys Phe Ala Ala Pro
            20                  25                  30

Ser Gln Lys Pro Arg Gly Thr Val Ile Leu Phe Tyr Val Glu Gly Ala
        35                  40                  45

Gly Arg Gly Val Thr Gly Gly His Ala Val Asn Tyr Asn Lys Gln Gly
    50                  55                  60

Thr Ser Ile His Ala Glu Val Leu Leu Leu Ser Ala Val Arg Ala Ala
65                  70                  75                  80

Leu Leu Arg Arg Arg Arg Cys Glu Asp Gly Glu Glu Ala Thr Arg Gly
                85                  90                  95

Cys Thr Leu His Cys Tyr Ser Thr Tyr Ser Pro Cys Arg Asp Cys Val
            100                 105                 110

Glu Tyr Ile Gln Glu Trp Tyr Asn Gln Glu Leu Arg Gly Asn Gly His
        115                 120                 125

Thr Leu Lys Ile Trp Ala Cys Lys Leu Tyr Tyr Glu Lys Asn Ala Arg
    130                 135                 140

Asn Gln Ile Gly Leu Trp Asn Leu Arg Asp Asn Gly Val Gly Leu Asn
145                 150                 155                 160

Val Met Val Ser Glu His Tyr Gln Cys Cys Arg Lys Ile Phe Ile Gln
                165                 170                 175

Ser Ser His Asn Gln Leu Asn Glu Asn Arg Trp Leu Glu Lys Thr Leu
            180                 185                 190

Lys Arg Ala Glu Lys Arg Arg Ser Glu Leu Ser Ile Met Ile Gln Val
        195                 200                 205

Lys Ile Leu His Thr Thr Lys Ser Pro Ala Val
    210                 215
```

```
<210> SEQ ID NO 7
<211> LENGTH: 87
<212> TYPE: PRT
<213> ORGANISM: Saccharomyces cerevisiae

<400> SEQUENCE: 7

Met Gln Leu Leu Arg Cys Phe Ser Ile Phe Ser Val Ile Ala Ser Val
1               5                   10                  15

Leu Ala Gln Glu Leu Thr Thr Ile Cys Glu Gln Ile Pro Ser Pro Thr
            20                  25                  30

Leu Glu Ser Thr Pro Tyr Ser Leu Ser Thr Thr Thr Ile Leu Ala Asn
        35                  40                  45

Gly Lys Ala Met Gln Gly Val Phe Glu Tyr Tyr Lys Ser Val Thr Phe
    50                  55                  60

Val Ser Asn Cys Gly Ser His Pro Ser Thr Thr Ser Lys Gly Ser Pro
65                  70                  75                  80

Ile Asn Thr Gln Tyr Val Phe
                85


<210> SEQ ID NO 8
<211> LENGTH: 725
<212> TYPE: PRT
<213> ORGANISM: Saccharomyces cerevisiae

<400> SEQUENCE: 8

Met Thr Leu Ser Phe Ala His Phe Thr Tyr Leu Phe Thr Ile Leu Leu
1               5                   10                  15

Gly Leu Thr Asn Ile Ala Leu Ala Ser Asp Pro Glu Thr Ile Leu Val
            20                  25                  30

Thr Ile Thr Lys Thr Asn Asp Ala Asn Gly Val Val Thr Thr Thr Val
        35                  40                  45

Ser Pro Ala Leu Val Ser Thr Ser Thr Ile Val Gln Ala Gly Thr Thr
    50                  55                  60

Thr Leu Tyr Thr Thr Trp Cys Pro Leu Thr Val Ser Thr Ser Ser Ala
65                  70                  75                  80

Ala Glu Ile Ser Pro Ser Ile Ser Tyr Ala Thr Thr Leu Ser Arg Phe
                85                  90                  95

Ser Thr Leu Thr Leu Ser Thr Glu Val Cys Ser His Glu Ala Cys Pro
            100                 105                 110

Ser Ser Ser Thr Leu Pro Thr Thr Thr Leu Ser Val Thr Ser Lys Phe
        115                 120                 125

Thr Ser Tyr Ile Cys Pro Thr Cys His Thr Thr Ala Ile Ser Ser Leu
    130                 135                 140

Ser Glu Val Gly Thr Thr Thr Val Val Ser Ser Ser Ala Ile Glu Pro
145                 150                 155                 160

Ser Ser Ala Ser Ile Ile Ser Pro Val Thr Ser Thr Leu Ser Ser Thr
                165                 170                 175

Thr Ser Ser Asn Pro Thr Thr Thr Ser Leu Ser Ser Thr Ser Thr Ser
            180                 185                 190

Pro Ser Ser Thr Ser Thr Ser Pro Ser Ser Thr Ser Thr Ser Ser Ser
        195                 200                 205

Ser Thr Ser Thr Ser Ser Ser Ser Thr Ser Thr Ser Ser Ser Ser Thr
    210                 215                 220

Ser Thr Ser Pro Ser Ser Thr Ser Thr Ser Ser Ser Leu Thr Ser Thr
225                 230                 235                 240

Ser Ser Ser Ser Thr Ser Thr Ser Gln Ser Ser Thr Ser Thr Ser Ser
```

```
                245                 250                 255

Ser Ser Thr Ser Thr Ser Pro Ser Ser Thr Ser Thr Ser Ser Ser Ser
            260                 265                 270

Thr Ser Thr Ser Pro Ser Ser Lys Ser Thr Ser Ala Ser Ser Thr Ser
        275                 280                 285

Thr Ser Ser Tyr Ser Thr Ser Thr Ser Pro Ser Leu Thr Ser Ser Ser
    290                 295                 300

Pro Thr Leu Ala Ser Thr Ser Pro Ser Ser Thr Ser Ile Ser Ser Thr
305                 310                 315                 320

Phe Thr Asp Ser Thr Ser Ser Leu Gly Ser Ser Ile Ala Ser Ser Ser
                325                 330                 335

Thr Ser Val Ser Leu Tyr Ser Pro Ser Thr Pro Val Tyr Ser Val Pro
            340                 345                 350

Ser Thr Ser Ser Asn Val Ala Thr Pro Ser Met Thr Ser Ser Thr Val
        355                 360                 365

Glu Thr Thr Val Ser Ser Gln Ser Ser Ser Glu Tyr Ile Thr Lys Ser
    370                 375                 380

Ser Ile Ser Thr Thr Ile Pro Ser Phe Ser Met Ser Thr Tyr Phe Thr
385                 390                 395                 400

Thr Val Ser Gly Val Thr Thr Met Tyr Thr Thr Trp Cys Pro Tyr Ser
                405                 410                 415

Ser Glu Ser Glu Thr Ser Thr Leu Thr Ser Met His Glu Thr Val Thr
            420                 425                 430

Thr Asp Ala Thr Val Cys Thr His Glu Ser Cys Met Pro Ser Gln Thr
        435                 440                 445

Thr Ser Leu Ile Thr Ser Ser Ile Lys Met Ser Thr Lys Asn Val Ala
    450                 455                 460

Thr Ser Val Ser Thr Ser Thr Val Glu Ser Ser Tyr Ala Cys Ser Thr
465                 470                 475                 480

Cys Ala Glu Thr Ser His Ser Tyr Ser Ser Val Gln Thr Ala Ser Ser
                485                 490                 495

Ser Ser Val Thr Gln Gln Thr Thr Ser Thr Lys Ser Trp Val Ser Ser
            500                 505                 510

Met Thr Thr Ser Asp Glu Asp Phe Asn Lys His Ala Thr Gly Lys Tyr
        515                 520                 525

His Val Thr Ser Ser Gly Thr Ser Thr Ile Ser Thr Ser Val Ser Glu
    530                 535                 540

Ala Thr Ser Thr Ser Ser Ile Asp Ser Glu Ser Gln Glu Gln Ser Ser
545                 550                 555                 560

His Leu Leu Ser Thr Ser Val Leu Ser Ser Ser Ser Leu Ser Ala Thr
                565                 570                 575

Leu Ser Ser Asp Ser Thr Ile Leu Leu Phe Ser Ser Val Ser Ser Leu
            580                 585                 590

Ser Val Glu Gln Ser Pro Val Thr Thr Leu Gln Ile Ser Ser Thr Ser
        595                 600                 605

Glu Ile Leu Gln Pro Thr Ser Ser Thr Ala Ile Ala Thr Ile Ser Ala
    610                 615                 620

Ser Thr Ser Ser Leu Ser Ala Thr Ser Ile Ser Thr Pro Ser Thr Ser
625                 630                 635                 640

Val Glu Ser Thr Ile Glu Ser Ser Ser Leu Thr Pro Thr Val Ser Ser
                645                 650                 655

Ile Phe Leu Ser Ser Ser Ser Ala Pro Ser Ser Leu Gln Thr Ser Val
            660                 665                 670
```

```
Thr Thr Thr Glu Val Ser Thr Thr Ser Ile Ser Ile Gln Tyr Gln Thr
        675                 680                 685

Ser Ser Met Val Thr Ile Ser Gln Tyr Met Gly Ser Gly Ser Gln Thr
    690                 695                 700

Arg Leu Pro Leu Gly Lys Leu Val Phe Ala Ile Met Ala Val Ala Cys
705                 710                 715                 720

Asn Val Ile Phe Ser
                725


<210> SEQ ID NO 9
<211> LENGTH: 6200
<212> TYPE: DNA
<213> ORGANISM: Artificial
<220> FEATURE:
<223> OTHER INFORMATION: Yeast Expression Vector

<400> SEQUENCE: 9

gaattttcaa aaattcttac tttttttttg gatggacgca aagaagttta ataatcatat     60

tacatggcat taccaccata tacatatcca tatacatatc catatctaat cttacttata    120

tgttgtggaa atgtaaagag ccccattatc ttagcctaaa aaaaccttct ctttggaact    180

ttcagtaata cgcttaactg ctcattgcta tattgaagta cggattagaa gccgccgagc    240

gggtgacagc cctccgaagg aagactctcc tccgtgcgtc ctcgtcttca ccggtcgcgt    300

tcctgaaacg cagatgtgcc tcgcgccgca ctgctccgaa caataaagat tctacaatac    360

tagcttttat ggttatgaag aggaaaaatt ggcagtaacc tggccccaca aaccttcaaa    420

tgaacgaatc aaattaacaa ccataggatg ataatgcgat tagtttttta gccttatttc    480

tggggtaatt aatcagcgaa gcgatgattt ttgatctatt aacagatata taaatgcaaa    540

aactgcataa ccactttaac taatactttc aacattttcg gtttgtatta cttcttattc    600

aaatgtaata aaagtatcaa caaaaaattg ttaatatacc tctatacttt aacgtcaagg    660

agaaaaaacc ccggatccat gcagttactt cgctgttttt caatattttc tgttattgct    720

tcagttttag cacaggaact gacaactata tgcgagcaaa tcccctcacc aactttagaa    780

tcgacgccgt actctttgtc aacgactact attttggcca acgggaaggc aatgcaagga    840

gtttttgaat attacaaatc agtaacgttt gtcagtaatt gcggttctca cccctcaaca    900

actagcaaag gcagccccat aaacacacag tatgtttttg gaggtggaga ttacaaggac    960

gacgatgaca agcgtggaag aggtagagga agagggggtg gaagatctca ggtgcagctg   1020

gtggagtctg gggaggctc ggtgcaggct ggagggtctc tgagactctc ctgtgcagcc   1080

tctggataca cctacagtaa ctactgcatg ggctggttcc gccaggctcc agggaaggag   1140

cgcgaggggg tcgcagttat tgatagtgat ggtagcacaa gctacgcaga ctccgtgaag   1200

ggccgattca ccatctccca agacaacgcc aagaacacgg tgtttctgca aatgaacagc   1260

ctgaaacctg aggacactgc catgtactac tgtgcggcag atgagggacc taggcgggac   1320

tattcaggct cttggtgtta tgacacagat atctactggg gccaggggac ccaggtcacc   1380

gtctcctcag ctagccggcc gggtggcggt ggaagcggtg gaggtggctc atacccatac   1440

gatgttccag attacgctaa ctagtgagct ccaattcgcc ctatagtgag tcgtattaca   1500

attcactggc cgtcgtttta caacgtcgtg actgggaaaa ccctggcgtt acccaactta   1560

atcgccttgc agcacatccc cccttcgcca gctggcgtaa tagcgaagag gcccgcaccg   1620

atcgcccttc ccaacagttg cgcagcctga atggcgaatg gcgcgacgcg ccctgtagcg   1680
```

```
gcgcattaag cgcggcgggt gtggtggtta cgcgcagcgt gaccgctaca cttgccagcg   1740
ccctagcgcc cgctcctttc gctttcttcc cttcctttct cgccacgttc gccggctttc   1800
cccgtcaagc tctaaatcgg gggctccctt tagggttccg atttagtgct ttacggcacc   1860
tcgaccccaa aaaacttgat tagggtgatg gttcacgtag tgggccatcg ccctgataga   1920
cggtttttcg ccctttgacg ttggagtcca cgttctttaa tagtggactc ttgttccaaa   1980
ctggaacaac actcaaccct atctcggtct attcttttga tttataaggg attttgccga   2040
tttcggccta ttggttaaaa aatgagctga tttaacaaaa atttaacgcg aattttaaca   2100
aaatattaac gtttacaatt tcctgatgcg gtattttctc cttacgcatc tgtgcggtat   2160
ttcacaccgc aggcaagtgc acaaacaata cttaaataaa tactactcag taataaccta   2220
tttcttagca tttttgacga aatttgctat tttgttagag tcttttacac catttgtctc   2280
cacacctccg cttacatcaa caccaataac gccatttaat ctaagcgcat caccaacatt   2340
ttctggcgtc agtccaccag ctaacataaa atgtaagctt tcggggctct cttgccttcc   2400
aacccagtca gaaatcgagt tccaatccaa aagttcacct gtcccacctg cttctgaatc   2460
aaacaaggga ataaacgaat gaggtttctg tgaagctgca ctgagtagta tgttgcagtc   2520
ttttggaaat acgagtcttt taataactgg caaaccgagg aactcttggt attcttgcca   2580
cgactcatct ccatgcagtt ggacgatatc aatgccgtaa tcattgacca gagccaaaac   2640
atcctcctta ggttgattac gaaacacgcc aaccaagtat ttcggagtgc ctgaactatt   2700
tttatatgct tttacaagac ttgaaatttt ccttgcaata accgggtcaa ttgttctctt   2760
tctattgggc acacatataa tacccagcaa gtcagcatcg gaatctagag cacattctgc   2820
ggcctctgtg ctctgcaagc cgcaaacttt caccaatgga ccagaactac ctgtgaaatt   2880
aataacagac atactccaag ctgcctttgt gtgcttaatc acgtatactc acgtgctcaa   2940
tagtcaccaa tgccctccct cttggccctc tccttttctt ttttcgaccg aattaattct   3000
taatcggcaa aaaaagaaaa gctccggatc aagattgtac gtaaggtgac aagctatttt   3060
tcaataaaga atatcttcca ctactgccat ctggcgtcat aactgcaaag tacacatata   3120
ttacgatgct gtctattaaa tgcttcctat attatatata tagtaatgtc gtttatggtg   3180
cactctcagt acaatctgct ctgatgccgc atagttaagc cagccccgac acccgccaac   3240
acccgctgac gcgccctgac gggcttgtct gctcccggca tccgcttaca gacaagctgt   3300
gaccgtctcc gggagctgca tgtgtcagag gttttcaccg tcatcaccga aacgcgcgag   3360
acgaaagggc ctcgtgatac gcctattttt ataggttaat gtcatgataa taatggtttc   3420
ttaggacgga tcgcttgcct gtaacttaca cgcgcctcgt atcttttaat gatggaataa   3480
tttgggaatt tactctgtgt ttatttattt ttatgttttg tatttggatt ttagaaagta   3540
aataaagaag gtagaagagt tacggaatga agaaaaaaaa ataaacaaag gtttaaaaaa   3600
tttcaacaaa aagcgtactt tacatatata tttattagac aagaaaagca gattaaatag   3660
atatacattc gattaacgat aagtaaaatg taaaatcaca ggattttcgt gtgtggtctt   3720
ctacacagac aagatgaaac aattcggcat taatacctga gagcaggaag agcaagataa   3780
aaggtagtat ttgttggcga tccccctaga gtcttttaca tcttcggaaa acaaaaacta   3840
ttttttcttt aatttctttt tttactttct atttttaatt tatatattta tattaaaaaa   3900
tttaaattat aattattttt atagcacgtg atgaaaagga cccaggtggc acttttcggg   3960
gaaatgtgcg cggaacccct atttgtttat ttttctaaat acattcaaat atgtatccgc   4020
tcatgagaca ataaccctga taaatgcttc aataatattg aaaaaggaag agtatgagta   4080
```

```
ttcaacattt ccgtgtcgcc cttattccct tttttgcggc attttgcctt cctgtttttg   4140
ctcacccaga aacgctggtg aaagtaaaag atgctgaaga tcagttgggt gcacgagtgg   4200
gttacatcga actggatctc aacagcggta agatccttga gagttttcgc cccgaagaac   4260
gttttccaat gatgagcact tttaaagttc tgctatgtgg cgcggtatta tcccgtattg   4320
acgccgggca agagcaactc ggtcgccgca tacactattc tcagaatgac ttggttgagt   4380
actcaccagt cacagaaaag catcttacgg atggcatgac agtaagagaa ttatgcagtg   4440
ctgccataac catgagtgat aacactgcgg ccaacttact tctgacaacg atcggaggac   4500
cgaaggagct aaccgctttt ttcacaaca tgggggatca tgtaactcgc cttgatcgtt   4560
gggaaccgga gctgaatgaa gccataccaa acgacgagcg tgacaccacg atgcctgtag   4620
caatggcaac aacgttgcgc aaactattaa ctggcgaact acttactcta gcttcccggc   4680
aacaattaat agactggatg gaggcggata aagttgcagg accacttctg cgctcggccc   4740
ttccggctgg ctggtttatt gctgataaat ctggagccgg tgagcgtggg tctcgcggta   4800
tcattgcagc actggggcca gatggtaagc cctcccgtat cgtagttatc tacacgacgg   4860
gcagtcaggc aactatggat gaacgaaata gacagatcgc tgagataggt gcctcactga   4920
ttaagcattg gtaactgtca gaccaagttt actcatatat actttagatt gatttaaaac   4980
ttcattttta atttaaaagg atctaggtga agatcctttt tgataatctc atgaccaaaa   5040
tcccttaacg tgagttttcg ttccactgag cgtcagaccc cgtagaaaag atcaaaggat   5100
cttcttgaga tcctttttt ctgcgcgtaa tctgctgctt gcaaacaaaa aaaccaccgc   5160
taccagcggt ggtttgtttg ccggatcaag agctaccaac tctttttccg aaggtaactg   5220
gcttcagcag agcgcagata ccaaatactg tccttctagt gtagccgtag ttaggccacc   5280
acttcaagaa ctctgtagca ccgcctacat acctcgctct gctaatcctg ttaccagtgg   5340
ctgctgccag tggcgataag tcgtgtctta ccgggttgga ctcaagacga tagttaccgg   5400
ataaggcgca gcggtcgggc tgaacggggg gttcgtgcac acagcccagc ttggagcgaa   5460
cgacctacac cgaactgaga tacctacagc gtgagcattg agaaagcgcc acgcttcccg   5520
aagggagaaa ggcggacagg tatccggtaa gcggcagggt cggaacagga gagcgcacga   5580
gggagcttcc agggggaaac gcctggtatc tttatagtcc tgtcgggttt cgccacctct   5640
gacttgagcg tcgatttttg tgatgctcgt caggggggcc gagcctatgg aaaaacgcca   5700
gcaacgcggc ctttttacgg ttcctggcct tttgctggcc ttttgctcac atgttctttc   5760
ctgcgttatc ccctgattct gtggataacc gtattaccgc ctttgagtga gctgataccg   5820
ctcgccgcag ccgaacgacc gagcgcagcg agtcagtgag cgaggaagcg gaagagcgcc   5880
caatacgcaa accgcctctc cccgcgcgtt ggccgattca ttaatgcagc tggcacgaca   5940
ggtttcccga ctggaaagcg ggcagtgagc gcaacgcaat taatgtgagt tacctcactc   6000
attaggcacc ccaggcttta cactttatgc ttccggctcc tatgttgtgt ggaattgtga   6060
gcggataaca atttcacaca ggaaacagct atgaccatga ttacgccaag ctcggaatta   6120
accctcacta aagggaacaa aagctgggta ccgggccccc cctcgaggtc gacggtatcg   6180
ataagcttga tatcgaattc                                               6200
```

<210> SEQ ID NO 10
<211> LENGTH: 8380
<212> TYPE: DNA
<213> ORGANISM: Artificial
<220> FEATURE:

<223> OTHER INFORMATION: Yeast Expression Vector

<400> SEQUENCE: 10

```
acgaaagggc ctcgtgatac gcctattttt ataggttaat gtcatgataa taatggtttc      60
ttagtatgat ccaatatcaa aggaaatgat agcattgaag gatgagacta atccaattga     120
ggagtggcag catatagaac agctaaaggg tagtgctgaa ggaagcatac gataccccgc     180
atggaatggg ataatatcac aggaggtact agactacctt tcatcctaca taaatagacg     240
catataagta cgcatttaag cataaacacg cactatgccg ttcttctcat gtatatatat     300
atacaggcaa cacgcagata taggtgcgac gtgaacagtg agctgtatgt gcgcagctcg     360
cgttgcattt tcggaagcgc tcgttttcgg aaacgctttg aagttcctat tccgaagttc     420
ctattctcta gaaagtatag gaacttcaga gcgcttttga aaaccaaaag cgctctgaag     480
acgcactttc aaaaaaccaa aaacgcaccg gactgtaacg agctactaaa atattgcgaa     540
taccgcttcc acaaacattg ctcaaaagta tctctttgct atatatctct gtgctatatc     600
cctatataac ctacccatcc acctttcgct ccttgaactt gcatctaaac tcgacctcta     660
catttttat gtttatctct agtattactc tttagacaaa aaaattgtag taagaactat      720
tcatagagtg aatcgaaaac aatacgaaaa tgtaaacatt tcctatacgt agtatataga     780
gacaaaatag aagaaaccgt tcataatttt ctgaccaatg aagaatcatc aacgctatca     840
ctttctgttc acaaagtatg cgcaatccac atcggtatag aatataatcg ggatgccttt     900
tatcttgaaa aaatgcaccc gcagcttcgc tagtaatcag taaacgcggg aagtggagtc     960
aggcttttt tatggaagag aaaatagaca ccaaagtagc cttcttctaa ccttaacgga     1020
cctacagtgc aaaaagttat caagagactg cattatagag cgcacaaagg agaaaaaaag    1080
taatctaaga tgctttgtta gaaaaatagc gctctcggga tgcatttttg tagaacaaaa    1140
aagaagtata gattctttgt tggtaaaata gcgctctcgc gttgcatttc tgttctgtaa    1200
aaatgcagct cagattcttt gtttgaaaaa ttagcgctct cgcgttgcat ttttgtttta    1260
caaaaatgaa gcacagattc ttcgttggta aaatagcgct ttcgcgttgc atttctgttc    1320
tgtaaaaatg cagctcagat tctttgtttg aaaaattagc gctctcgcgt tgcatttttg    1380
ttctacaaaa tgaagcacag atgcttcgtt caggtggcac ttttcgggga aatgtgcgcg    1440
gaacccctat ttgtttattt ttctaaatac attcaaatat gtatccgctc atgagacaat    1500
aaccctgata aatgcttcaa taatattgaa aaaggaagag tatgagtatt caacatttcc    1560
gtgtcgccct tattcccttt tttgcggcat tttgccttcc tgtttttgct cacccagaaa    1620
cgctggtgaa agtaaaagat gctgaagatc agttgggtgc acgagtgggt tacatcgaac    1680
tggatctcaa cagcggtaag atccttgaga gttttcgccc cgaagaacgt tttccaatga    1740
tgagcacttt taaagttctg ctatgtggcg cggtattatc ccgtattgac gccgggcaag    1800
agcaactcgg tcgccgcata cactattctc agaatgactt ggttgagtac tcaccagtca    1860
cagaaaagca tcttacggat ggcatgacag taagagaatt atgcagtgct gccataacca    1920
tgagtgataa cactgcggcc aacttacttc tgacaacgat cggaggaccg aaggagctaa    1980
ccgctttttt gcacaacatg ggggatcatg taactcgcct tgatcgttgg gaaccggagc    2040
tgaatgaagc cataccaaac gacgagcgtg acaccacgat gcctgtagca atggcaacaa    2100
cgttgcgcaa actattaact ggcgaactac ttactctagc ttcccggcaa caattaatag    2160
actggatgga ggcggataaa gttgcaggac cacttctgcg ctcggccctt ccggctggct    2220
ggtttattgc tgataaatct ggagccggtg agcgtgggtc tcgcggtatc attgcagcac    2280
```

```
tggggccaga tggtaagccc tcccgtatcg tagttatcta cacgacgggg agtcaggcaa   2340
ctatggatga acgaaataga cagatcgctg agataggtgc ctcactgatt aagcattggt   2400
aactgtcaga ccaagtttac tcatatatac tttagattga tttaaaactt catttttaat   2460
ttaaaaggat ctaggtgaag atcctttttg ataatctcat gaccaaaatc ccttaacgtg   2520
agttttcgtt ccactgagcg tcagaccccg tagaaaagat caaaggatct tcttgagatc   2580
cttttttttct gcgcgtaatc tgctgcttgc aaacaaaaaa accaccgcta ccagcggtgg   2640
tttgtttgcc ggatcaagag ctaccaactc tttttccgaa ggtaactggc ttcagcagag   2700
cgcagatacc aaatactgtc cttctagtgt agccgtagtt aggccaccac ttcaagaact   2760
ctgtagcacc gcctacatac ctcgctctgc taatcctgtt accagtggct gctgccagtg   2820
gcgataagtc gtgtcttacc gggttggact caagacgata gttaccggat aaggcgcagc   2880
ggtcgggctg aacggggggt tcgtgcacac agcccagctt ggagcgaacg acctacaccg   2940
aactgagata cctacagcgt gagctatgag aaagcgccac gcttcccgaa gggagaaagg   3000
cggacaggta tccggtaagc ggcagggtcg gaacaggaga gcgcacgagg gagcttccag   3060
ggggaaacgc ctggtatctt tatagtcctg tcgggtttcg ccacctctga cttgagcgtc   3120
gatttttgtg atgctcgtca ggggggcgga gcctatggaa aaacgccagc aacgcggcct   3180
ttttacggtt cctggccttt tgctggcctt ttgctcacat gttctttcct gcgttatccc   3240
ctgattctgt ggataaccgt attaccgcct ttgagtgagc tgataccgct cgccgcagcc   3300
gaacgaccga gcgcagcgag tcagtgagcg aggaagcgga agagcgccca atacgcaaac   3360
cgcctctccc cgcgcgttgg ccgattcatt aatgcagctg gatcttcgag cgtcccaaaa   3420
ccttctcaag caaggttttc agtataatgt tacatgcgta cacgcgtctg tacagaaaaa   3480
aaagaaaaat ttgaaatata aataacgttc ttaatactaa cataactata aaaaaataaa   3540
tagggaccta gacttcaggt tgtctaactc cttccttttc ggttagagcg gatcttagct   3600
agccgcggta ccaagcttac tcgaggtctt cttcggaaat caacttctgt tccatgtcga   3660
cgcccgggcc ctatagtgag tcgtattacg gatccggggt tttttctcct tgacgttaaa   3720
gtatagaggt atattaacaa ttttttgttg atacttttat tacatttgaa taagaagtaa   3780
tacaaaccga aaatgttgaa agtattagtt aaagtggtta tgcagttttt gcatttatat   3840
atctgttaat agatcaaaaa tcatcgcttc gctgattaat taccccagaa ataaggctaa   3900
aaaactaatc gcattatcat cctatggttg ttaatttgat tcgttcattt gaaggtttgt   3960
ggggccaggt tactgccaat ttttcctctt cataaccata aaagctagta ttgtagaatc   4020
tttattgttc ggagcagtgc ggcgcgaggc acatctgcgt ttcaggaacg cgaccggtga   4080
agacgaggac gcacggagga gagtcttcct tcggagggct gtcacccgct cggcggcttc   4140
taatccgtac ttcaatatag caatgagcag ttaagcgtat tactgaaagt tccaaagaga   4200
aggttttttt aggctaagat aatggggctc tttacatttc cacaacatat aagtaagatt   4260
agatatggat atgtatatgg atatgtatat ggtggtaatg ccatgtaata tgattattaa   4320
acttctttgc gtccatccaa aaaaaaagta agaatttttg aaaattcgaa ttcaaccctc   4380
actaaagggc ggccgcatga ccgacgctga gtacgtgaga atccatgaga agttggacat   4440
ctacacgttt aagaaacagt ttttcaacaa caaaaaatcc gtgtcgcata gatgctacgt   4500
tctctttgaa ttaaaacgac ggggtgaacg tagagcgtgt tttggggct atgctgtgaa   4560
taaaccacag agcgggacag aacgtggaat tcacgccgaa atctttagca ttagaaaagt   4620
```

-continued

```
cgaagaatac ctgcgcgaca accccggaca attcacgata aattggtact catcctggag   4680
tccttgtgca gattgcgctg aaaagatctt agaatggtat aaccaggagc tgcgggggaa   4740
cggccacact ttgaaaatct gggcttgcaa actctattac gagaaaaatg cgaggaatca   4800
aattgggctg tggaacctca gagataacgg ggttgggttg aatgtaatgg taagtgaaca   4860
ctaccaatgt tgcaggaaaa tattcatcca atcgtcgcac aatcaattga atgagaatag   4920
atggcttgag aagactttga agcgagctga aaaacgacgg agcgagttgt ccattatgat   4980
tcaggtaaaa atactccaca ccactaagag tcctgctgta ctagtatcga tggattacaa   5040
ggatgacgac gataagatct gagctcttaa ttaacaattc ttcgccagag gtttggtcaa   5100
gtctccaatc aaggttgtcg gcttgtctac cttgccagaa atttacgaaa agatggaaaa   5160
gggtcaaatc gttggtagat acgttgttga cacttctaaa taagcgaatt tcttatgatt   5220
tatgattttt attattaaat aagttataaa aaaaataagt gtatacaaat tttaaagtga   5280
ctcttaggtt ttaaaacgaa aattcttatt cttgagtaac tctttcctgt aggtcaggtt   5340
gctttctcag gtatagcatg aggtcgctcc aattcagctg gcgtaatagc gaagaggccc   5400
gcaccgatcg cccttcccaa cagttgcgca gcctgaatgg cgaatggcgc gacgcgccct   5460
gtagcggcgc attaagcgcg gcgggtgtgg tggttacgcg cagcgtgacc gctacacttg   5520
ccagcgccct agcgcccgct cctttcgctt tcttcccttc ctttctcgcc acgttcgccg   5580
gctttccccg tcaagctcta aatcgggggc tccctttagg gttccgattt agtgctttac   5640
ggcacctcga ccccaaaaaa cttgattagg gtgatggttc acgtagtggg ccatcgccct   5700
gatagacggt ttttcgccct ttgacgttgg agtccacgtt ctttaatagt ggactcttgt   5760
tccaaactgg aacaacactc aaccctatct cggtctattc ttttgattta taagggattt   5820
tgccgatttc ggcctattgg ttaaaaaatg agctgattta acaaaaattt aacgcgaatt   5880
ttaacaaaat attaacgttt acaatttcct gatgcggtat tttctcctta cgcatctgtg   5940
cggtatttca caccgcatat cgacggtcga ggagaacttc tagtatatcc acatacctaa   6000
tattattgcc ttattaaaaa tggaatccca acaattacat caaaatccac attctcttca   6060
aaatcaattg tcctgtactt ccttgttcat gtgtgttcaa aaacgttata tttataggat   6120
aattatactc tatttctcaa caagtaattg gttgtttggc cgagcggtct aaggcgcctg   6180
attcaagaaa tatcttgacc gcagttaact gtgggaatac tcaggtatcg taagatgcaa   6240
gagttcgaat ctcttagcaa ccattatttt tttcctcaac ataacgagaa cacacagggg   6300
cgctatcgca cagaatcaaa ttcgatgact ggaaattttt tgttaatttc agaggtcgcc   6360
tgacgcatat accttttca actgaaaaat tgggagaaaa aggaaaggtg agaggccgga   6420
accggctttt catatagaat agagaagcgt tcatgactaa atgcttgcat cacaatactt   6480
gaagttgaca atattattta aggacctatt gttttttcca ataggtggtt agcaatcgtc   6540
ttactttcta acttttctta ccttttacat ttcagcaata tatatatata tttcaaggat   6600
ataccattct aatgtctgcc cctatgtctg cccctaagaa gatcgtcgtt ttgccaggtg   6660
accacgttgg tcaagaaatc acagccgaag ccattaaggt tcttaaagct atttctgatg   6720
ttcgttccaa tgtcaagttc gatttcgaaa atcatttaat tggtggtgct gctatcgatg   6780
ctacaggtgt cccacttcca gatgaggcgc tggaagcctc caagaaggtt gatgccgttt   6840
tgttaggtgc tgtggctggt cctaaatggg gtaccggtag tgttagacct gaacaaggtt   6900
tactaaaaat ccgtaaagaa cttcaattgt acgccaactt aagaccatgt aactttgcat   6960
ccgactctct tttagactta tctccaatca agccacaatt tgctaaaggt actgacttcg   7020
```

```
ttgttgtcag agaattagtg ggaggtattt actttggtaa gagaaaggaa gacgatggtg   7080
atggtgtcgc ttgggatagt gaacaataca ccgttccaga agtgcaaaga atcacaagaa   7140
tggccgcttt catggcccta caacatgagc caccattgcc tatttggtcc ttggataaag   7200
ctaatctttt ggcctcttca agattatgga gaaaaactgt ggaggaaacc atcaagaacg   7260
aattccctac attgaaggtt caacatcaat tgattgattc tgccgccatg atcctagtta   7320
agaacccaac ccacctaaat ggtattataa tcaccagcaa catgtttggt gatatcatct   7380
ccgatgaagc ctccgttatc ccaggttcct tgggtttgtt gccatctgcg tccttggcct   7440
ctttgccaga caagaacacc gcatttggtt tgtacgaacc atgccacggt tctgctccag   7500
atttgccaaa gaataaggtt gaccctatcg ccactatctt gtctgctgca atgatgttga   7560
aattgtcatt gaacttgcct gaagaaggta aggccattga agatgcagtt aaaaaggttt   7620
tggatgcagg tatcagaact ggtgatttag gtggttccaa cagtaccacc gaagtcggtg   7680
atgctgtcgc cgaagaagtt aagaaaatcc ttgcttaaaa agattctctt tttttatgat   7740
atttgtacat aaactttata aatgaaattc ataatagaaa cgacacgaaa ttacaaaatg   7800
gaatatgttc atagggtaga cgaaactata tacgcaatct acatacattt atcaagaagg   7860
agaaaaagga ggatagtaaa ggaatacagg taagcaaatt gatactaatg gctcaacgtg   7920
ataaggaaaa agaattgcac tttaacatta atattgacaa ggaggagggc accacacaaa   7980
aagttaggtg taacagaaaa tcatgaaact acgattccta atttgatatt ggaggatttt   8040
ctctaaaaaa aaaaaaatac aacaaataaa aaacactcaa tgacctgacc atttgatgga   8100
gtttaagtca ataccttctt gaagcatttc ccataatggt gaaagttccc tcaagaattt   8160
tactctgtca gaaacggcct tacgacgtag tcgatatggt gcactctcag tacaatctgc   8220
tctgatgccg catagttaag ccagccccga cacccgccaa cacccgctga cgcgccctga   8280
cgggcttgtc tgctcccggc atccgcttac agacaagctg tgaccgtctc cgggagctgc   8340
atgtgtcaga ggttttcacc gtcatcaccg aaacgcgcga                         8380
```

<210> SEQ ID NO 11
<211> LENGTH: 7567
<212> TYPE: DNA
<213> ORGANISM: Artificial
<220> FEATURE:
<223> OTHER INFORMATION: Yeast Expression Vector

<400> SEQUENCE: 11

```
gtagtatata gagacaaaat agaagaaacc gttcataatt ttctgaccaa tgaagaatca     60
tcaacgctat cactttctgt tcacaaagta tgcgcaatcc acatcggtat agaatataat    120
cggggatgcc tttatcttga aaaaatgcac ccgcagcttc gctagtaatc agtaaacgcg    180
ggaagtggag tcaggctttt tttatggaag agaaaataga caccaaagta gccttcttct    240
aaccttaacg gacctacagt gcaaaaagtt atcaagagac tgcattatag agcgcacaaa    300
ggagaaaaaa agtaatctaa gatgctttgt tagaaaaata gcgctctcgg gatgcatttt    360
tgtagaacaa aaaagaagta tagattcttt gttggtaaaa tagcgctctc gcgttgcatt    420
tctgttctgt aaaaatgcag ctcagattct ttgtttgaaa aattagcgct ctcgcgttgc    480
atttttgttt tacaaaaatg aagcacagat tcttcgttgg taaaatagcg ctttcgcgtt    540
gcatttctgt tctgtaaaaa tgcagctcag attctttgtt tgaaaaatta gcgctctcgc    600
gttgcatttt tgttctacaa aatgaagcac agatgcttcg ttcaggtggc acttttcggg    660
```

-continued

```
gaaatgtgcg cggaacccct atttgtttat ttttctaaat acattcaaat atgtatccgc    720
tcatgagaca ataaccctga taaatgcttc aataatattg aaaaaggaag agtatgagta    780
ttcaacattt ccgtgtcgcc cttattccct tttttgcggc attttgcctt cctgtttttg    840
ctcacccaga aacgctggtg aaagtaaaag atgctgaaga tcagttgggt gcacgagtgg    900
gttacatcga actggatctc aacagcggta agatccttga gagttttcgc cccgaagaac    960
gttttccaat gatgagcact tttaaagttc tgctatgtgg cgcggtatta tcccgtattg   1020
acgccgggca agagcaactc ggtcgccgca tacactattc tcagaatgac ttggttgagt   1080
actcaccagt cacagaaaag catcttacgg atggcatgac agtaagagaa ttatgcagtg   1140
ctgccataac catgagtgat aacactgcgg ccaacttact tctgacaacg atcggaggac   1200
cgaaggagct aaccgctttt ttgcacaaca tgggggatca tgtaactcgc cttgatcgtt   1260
gggaaccgga gctgaatgaa gccataccaa acgacgagcg tgacaccacg atgcctgtag   1320
caatggcaac aacgttgcgc aaactattaa ctggcgaact acttactcta gcttcccggc   1380
aacaattaat agactggatg gaggcggata aagttgcagg accacttctg cgctcggccc   1440
ttccggctgg ctggtttatt gctgataaat ctggagccgg tgagcgtggg tctcgcggta   1500
tcattgcagc actggggcca gatggtaagc cctcccgtat cgtagttatc tacacgacgg   1560
ggagtcaggc aactatggat gaacgaaata gacagatcgc tgagataggt gcctcactga   1620
ttaagcattg gtaactgtca gaccaagttt actcatatat actttagatt gatttaaaac   1680
ttcattttta atttaaaagg atctaggtga agatcctttt tgataatctc atgaccaaaa   1740
tcccttaacg tgagttttcg ttccactgag cgtcagaccc cgtagaaaag atcaaaggat   1800
cttcttgaga tccttttttt ctgcgcgtaa tctgctgctt gcaaacaaaa aaaccaccgc   1860
taccagcggt ggtttgtttg ccggatcaag agctaccaac tctttttccg aaggtaactg   1920
gcttcagcag agcgcagata ccaaatactg tccttctagt gtagccgtag ttaggccacc   1980
acttcaagaa ctctgtagca ccgcctacat acctcgctct gctaatcctg ttaccagtgg   2040
ctgctgccag tggcgataag tcgtgtctta ccgggttgga ctcaagacga tagttaccgg   2100
ataaggcgca gcggtcgggc tgaacggggg gttcgtgcac acagcccagc ttggagcgaa   2160
cgacctacac cgaactgaga tacctacagc gtgagctatg agaaagcgcc acgcttcccg   2220
aagggagaaa ggcggacagg tatccggtaa gcggcagggt cggaacagga gagcgcacga   2280
gggagcttcc agggggaaac gcctggtatc tttatagtcc tgtcgggttt cgccacctct   2340
gacttgagcg tcgatttttg tgatgctcgt caggggggcg gagcctatgg aaaaacgcca   2400
gcaacgcggc ctttttacgg ttcctggcct tttgctggcc ttttgctcac atgttctttc   2460
ctgcgttatc ccctgattct gtggataacc gtattaccgc ctttgagtga gctgataccg   2520
ctcgccgcag ccgaacgacc gagcgcagcg agtcagtgag cgaggaagcg gaagagcgcc   2580
caatacgcaa accgcctctc cccgcgcgtt ggccgattca ttaatgcagc tggatcttcg   2640
agcgtcccaa aaccttctca agcaaggttt tcagtataat gttacatgcg tacacgcgtc   2700
tgtacagaaa aaaaagaaaa atttgaaata taaataacgt tcttaatact aacataacta   2760
taaaaaaata aatagggacc tagacttcag gttgtctaac tccttccttt tcggttagag   2820
cggatcttag ctagccgcgg taccaagctt actcgaggtc ttcttcggaa atcaacttct   2880
gttccatgtc gacgcccggg ccctatagtg agtcgtatta cggatccggg gtttttctc    2940
cttgacgtta aagtatagag gtatattaac aatttttttgt tgatactttt attacatttg  3000
aataagaagt aatacaaacc gaaaatgttg aaagtattag ttaaagtggt tatgcagttt   3060
```

```
ttgcatttat atatctgtta atagatcaaa aatcatcgct tcgctgatta attaccccag   3120
aaataaggct aaaaaactaa tcgcattatc atcctatggt tgttaatttg attcgttcat   3180
ttgaaggttt gtggggccag gttactgcca atttttcctc ttcataacca taaaagctag   3240
tattgtagaa tctttattgt tcggagcagt gcggcgcgag gcacatctgc gtttcaggaa   3300
cgcgaccggt gaagacgagg acgcacggag gagagtcttc cttcggaggg ctgtcacccg   3360
ctcggcggct tctaatccgt acttcaatat agcaatgagc agttaagcgt attactgaaa   3420
gttccaaaga gaaggttttt ttaggctaag ataatggggc tctttacatt tccacaacat   3480
ataagtaaga ttagatatgg atatgtatat ggatatgtat atggtggtaa tgccatgtaa   3540
tatgattatt aaacttcttt gcgtccatcc aaaaaaaaag taagaatttt tgaaaattcg   3600
aattcaaccc tcactaaagg gcggccgcat gaccgacgct gagtacgtga gaatccatga   3660
gaagttggac atctacacgt ttaagaaaca gtttttcaac aacaaaaaat ccgtgtcgca   3720
tagatgctac gttctctttg aattaaaacg acggggtgaa cgtagagcgt gtttttgggg   3780
ctatgctgtg aataaaccac agagcgggac agaacgtgga attcacgccg aaatctttag   3840
cattagaaaa gtcgaagaat acctgcgcga caaccccgga caattcacga taaattggta   3900
ctcatcctgg agtccttgtg cagattgcgc tgaaaagatc ttagaatggt ataaccagga   3960
gctgcggggg aacggccaca ctttgaaaat ctgggcttgc aaactctatt acgagaaaaa   4020
tgcgaggaat caaattgggc tgtggaacct cagagataac ggggttgggt tgaatgtaat   4080
ggtaagtgaa cactaccaat gttgcaggaa aatattcatc caatcgtcgc acaatcaatt   4140
gaatgagaat agatggcttg agaagacttt gaagcgagct gaaaaacgac ggagcgagtt   4200
gtccattatg attcaggtaa aaatactcca caccactaag agtcctgctg tactagtatc   4260
gatggattac aaggatgacg acgataagat ctgagctctt aattaacaat tcttcgccag   4320
aggtttggtc aagtctccaa tcaaggttgt cggcttgtct accttgccag aaatttacga   4380
aaagatggaa aagggtcaaa tcgttggtag atacgttgtt gacacttcta aataagcgaa   4440
tttcttatga tttatgattt ttattattaa ataagttata aaaaaaataa gtgtatacaa   4500
attttaaagt gactcttagg ttttaaaacg aaaattctta ttcttgagta actctttcct   4560
gtaggtcagg ttgctttctc aggtatagca tgaggtcgct ccaattcagc tggcgtaata   4620
gcgaagaggc ccgcaccgat cgcccttccc aacagttgcg cagcctgaat ggcgaatggc   4680
gcgacgcgcc ctgtagcggc gcattaagcg cggcgggtgt ggtggttacg cgcagcgtga   4740
ccgctacact tgccagcgcc ctagcgcccg ctcctttcgc tttcttccct tcctttctcg   4800
ccacgttcgc cggctttccc cgtcaagctc taaatcgggg gctcccttta gggttccgat   4860
ttagtgcttt acggcacctc gaccccaaaa aacttgatta gggtgatggt tcacgtagtg   4920
ggccatcgcc ctgatagacg gtttttcgcc ctttgacgtt ggagtccacg ttctttaata   4980
gtggactctt gttccaaact ggaacaacac tcaaccctat ctcggtctat tcttttgatt   5040
tataagggat tttgccgatt tcggcctatt ggttaaaaaa tgagctgatt taacaaaaat   5100
ttaacgcgaa ttttaacaaa atattaacgt ttacaatttc ctgatgcggt attttctcct   5160
tacgcatctg tgcggtattt cacaccgcat atcgacggtc gaggagaact tctagtatat   5220
ccacatacct aatattattg ccttattaaa aatggaatcc caacaattac atcaaaatcc   5280
acattctctt caaaatcaat tgtcctgtac ttccttgttc atgtgtgttc aaaaacgtta   5340
tatttatagg ataattatac tctatttctc aacaagtaat tggttgtttg gccgagcggt   5400
```

```
ctaaggcgcc tgattcaaga aatatcttga ccgcagttaa ctgtgggaat actcaggtat   5460
cgtaagatgc aagagttcga atctcttagc aaccattatt tttttcctca acataacgag   5520
aacacacagg ggcgctatcg cacagaatca aattcgatga ctggaaattt tttgttaatt   5580
tcagaggtcg cctgacgcat ataccttttt caactgaaaa attgggagaa aaaggaaagg   5640
tgagaggccg gaaccggctt ttcatataga atagagaagc gttcatgact aaatgcttgc   5700
atcacaatac ttgaagttga caatattatt taaggaccta ttgtttttttc caataggtgg   5760
ttagcaatcg tcttactttc taacttttct taccttttac atttcagcaa tatatatata   5820
tatttcaagg atataccatt ctaatgtctg cccctatgtc tgcccctaag aagatcgtcg   5880
ttttgccagg tgaccacgtt ggtcaagaaa tcacagccga agccattaag gttcttaaag   5940
ctatttctga tgttcgttcc aatgtcaagt tcgatttcga aaatcattta attggtggtg   6000
ctgctatcga tgctacaggt gtcccacttc cagatgaggc gctggaagcc tccaagaagg   6060
ttgatgccgt tttgttaggt gctgtggctg gtcctaaatg gggtaccggt agtgttagac   6120
ctgaacaagg tttactaaaa atccgtaaag aacttcaatt gtacgccaac ttaagaccat   6180
gtaactttgc atccgactct cttttagact tatctccaat caagccacaa tttgctaaag   6240
gtactgactt cgttgttgtc agagaattag tgggaggtat ttactttggt aagagaaagg   6300
aagacgatgg tgatggtgtc gcttgggata gtgaacaata caccgttcca gaagtgcaaa   6360
gaatcacaag aatggccgct ttcatggccc tacaacatga gccaccattg cctatttggt   6420
ccttggataa agctaatctt ttggcctctt caagattatg gagaaaaact gtggaggaaa   6480
ccatcaagaa cgaattccct acattgaagg ttcaacatca attgattgat tctgccgcca   6540
tgatcctagt taagaaccca acccacctaa atggtattat aatcaccagc aacatgtttg   6600
gtgatatcat ctccgatgaa gcctccgtta tcccaggttc cttgggtttg ttgccatctg   6660
cgtccttggc ctctttgcca gacaagaaca ccgcatttgg tttgtacgaa ccatgccacg   6720
gttctgctcc agatttgcca aagaataagg ttgaccctat cgccactatc ttgtctgctg   6780
caatgatgtt gaaattgtca ttgaacttgc ctgaagaagg taaggccatt gaagatgcag   6840
ttaaaaaggt tttggatgca ggtatcagaa ctggtgattt aggtggttcc aacagtacca   6900
ccgaagtcgg tgatgctgtc gccgaagaag ttaagaaaat ccttgcttaa aaagattctc   6960
ttttttttatg atatttgtac ataaacttta taaatgaaat tcataataga aacgacacga   7020
aattacaaaa tggaatatgt tcatagggta gacgaaacta tatacgcaat ctacatacat   7080
ttatcaagaa ggagaaaaag gaggatagta aaggaataca ggtaagcaaa ttgatactaa   7140
tggctcaacg tgataaggaa aaagaattgc actttaacat taatattgac aaggaggagg   7200
gcaccacaca aaaagttagg tgtaacagaa aatcatgaaa ctacgattcc taatttgata   7260
ttggaggatt ttctctaaaa aaaaaaaaat acaacaaata aaaaacactc aatgacctga   7320
ccatttgatg gagtttaagt caataccttc ttgaagcatt tcccataatg gtgaaagttc   7380
cctcaagaat tttactctgt cagaaacggc cttacgacgt agtcgatatg gtgcactctc   7440
agtacaatct gctctgatgc cgcatagtta agccagcccc gacacccgcc aacacccgct   7500
gacgcgccct gacgggcttg tctgctcccg gcatccgctt acagacaagc tgtgaccgtc   7560
tccggga                                                             7567
```

```
<210> SEQ ID NO 12
<211> LENGTH: 7312
<212> TYPE: DNA
<213> ORGANISM: Artificial
```

<220> FEATURE:
<223> OTHER INFORMATION: Yeast Expression Vector

<400> SEQUENCE: 12

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcgggggc tccctttagg    180
gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta taagggattt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg agacaataac cctgataaat gcttcaataa tattgaaaaa ggaagagtat    600
gagtattcaa catttccgtg tcgcccttat tccctttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca caacatgggg gatcatgtaa ctcgccttga   1080
tcgttgggaa ccggagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380
gacggggagt caggcaacta tggatgaacg aaatagacag atcgctgaga taggtgcctc   1440
actgattaag cattggtaac tgtcagacca agtttactca tatatacttt agattgattt   1500
aaaacttcat ttttaattta aaaggatcta ggtgaagatc ctttttgata atctcatgac   1560
caaaatccct taacgtgagt tttcgttcca ctgagcgtca gaccccgtag aaaagatcaa   1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
```

```
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
tttttcctg tttggtcact gatgcctccg tgtaaggggg atttctgttc atgggggtaa   2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg gcgataatgg cctgcttctc gccgaaacgt ttggtggcgg   3360
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcaggc gaaaatcctg tttgatggtg gttaacggcg ggatataaca tgagctgtct   3900
tcggtatcgt cgtatcccac taccgagata tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa aataatactg   4260
ttgatgggtg tctggtcaga gacatcaaga aataacgccg gaacattagt gcaggcagct   4320
tccacagcaa tggcatcctg gtcatccagc ggatagttaa tgatcagccc actgacgcgt   4380
tgcgcgagaa gattgtgcac cgccgcttta caggcttcga cgccgcttcg ttctaccatc   4440
gacaccacca cgctggcacc cagttgatcg gcgcgagatt taatcgccgc gacaatttgc   4500
gacggcgcgt gcagggccag actggaggtg gcaacgccaa tcagcaacga ctgtttgccc   4560
gccagttgtt gtgccacgcg gttgggaatg taattcagct ccgccatcgc cgcttccact   4620
```

```
ttttcccgcg ttttcgcaga aacgtggctg gcctggttca ccacgcggga aacggtctga   4680
taagagacac cggcatactc tgcgacatcg tataacgtta ctggtttcac attcaccacc   4740
ctgaattgac tctcttccgg gcgctatcat gccataccgc gaaaggtttt gcgccattcg   4800
atggtgtccg ggatctcgac gctctccctt atgcgactcc tgcattagga agcagcccag   4860
tagtaggttg aggccgttga gcaccgccgc cgcaaggaat ggtgcatgca aggagatggc   4920
gcccaacagt cccccggcca cggggcctgc caccataccc acgccgaaac aagcgctcat   4980
gagcccgaag tggcgagccc gatcttcccc atcggtgatg tcggcgatat aggcgccagc   5040
aaccgcacct gtggcgccgg tgatgccggc cacgatgcgt ccggcgtaga ggatcgagat   5100
ctcgatcccg cgaaattaat acgactcact ataggggaat tgtgagcgga taacaattcc   5160
cctctagaaa taattttgtt taactttaag aaggagatat acatatgaaa aagacggcaa   5220
ttgccatcgc agtggctctg gcaggatttg cgacagtagc ccaggctgag gttcagctgg   5280
tggaatcagg tggtggtctg gttcagccag gaggctctct ccgcttgtcg tgtgctgctt   5340
cggggtatga cttcacccac tatgggatga attgggtacg tcaagcacct ggcaaaggac   5400
ttgagtgggt aggctggatt aacacctata caggtgaacc gacctatgcc gcagacttta   5460
aacgccgctt tacgttttcc ctggatacca gcaagagtac ggcgtatctg cagatgaaca   5520
gcttacgtgc ggaagatacg gcggtctatt actgcgccaa atacccgtac tactatggca   5580
ctagccattg gtacttcgat gtgtggggtc aaggcactct ggtcaccgtg tcctcagcgt   5640
cgaccaaggg cccatcggtc ttccccctgg caccctcctc caagagcacc tctgggggca   5700
cagcggccct gggctgcctg gtcaaggact acttccccga acctgtgacg gtctcgtgga   5760
actcaggcgc cctgaccagc ggcgtgcaca ccttcccggc tgtcctacag tcctcaggac   5820
tctactccct cagcagcgtg gtgaccgtgc cctccagcag cttgggcacc cagacctaca   5880
tctgcaacgt gaatcacaag cccagcaaca ccaaggtgga caagaaagtt gagcccaaat   5940
cttgtgacaa aactcaccac caccaccacc acaccggtgg tggcggcggt tctggaggtg   6000
gcggttctgg aggcggtggc tctgtgcagc tggtggagtc tgggggaggc tcggtgcagg   6060
ctggagggtc tctgagactc tcctgtgcag cctccggata cacctacagt aggtactgca   6120
tgggctggtt ccgccaggct ccagggaagg agcgcgaggg ggtcgcagct attgatagta   6180
atggtcacac aaggtacgta gactccaaga agggccgatt caccatctcc aaagacaacg   6240
ccaagaacac tctgtatctg caaatgaacg gcctgaaacc tgaggatact gccatgtact   6300
actgtgcggc agaccccgtg ggtggtagga ggcccaatca gtttgaatac tggggccagg   6360
gcacccaggt caccgtctcc tcagctagcg gatccgatta caaggacgac gatgacaagt   6420
aacatggaga aaataaaatg aaatacctgc tgccgaccgc tgctgctggt ctgctgctcc   6480
tcgctgccca gccggcgatg gccgacattc agctgactca gagtccttcc agcttaagcg   6540
catctgttgg cgatcgtgtg acgattacgt gtagtgcctc gcaagacatc tccaactacc   6600
tgaattggta tcagcagaaa ccgggcaaag ctccgaaagt cctgatctac ttcacctcat   6660
cgctgcatag cggtgtacca agtcgcttta gcggttctgg ctcaggtacc gatttcaccc   6720
tcacgattag ctcgttgcaa cccgaagatt ttgcgaccta ttactgccag cagtattcca   6780
ctgttccgtg gacctttgga caagggacaa aggtggagat caaacgtacg gtggctgcac   6840
catctgtctt catcttcccg ccatctgatg agcagttgaa atctggaact gcctctgttg   6900
tgtgcctgct gaataacttc tatcccagag aggccaaagt acagtggaag gtggataacg   6960
```

```
ccctccaatc gggtaactcc caggagagtg tcacagagca ggacagcaag gacagcacct   7020

acagcctcag cagcaccctg acgctgagca aagcagacta cgagaaacac aaagtctacg   7080

cctgcgaagt cacccatcag ggcctgagct cgcccgtcac aaagagcttc aacaggggag   7140

agtgttaaac tcgagcacca ccaccaccac cactgagatc cggctgctaa caaagcccga   7200

aaggaagctg agttggctgc tgccaccgct gagcaataac tagcataacc ccttggggcc   7260

tctaaacggg tcttgagggg ttttttgctg aaaggaggaa ctatatccgg at           7312


<210> SEQ ID NO 13
<211> LENGTH: 9100
<212> TYPE: DNA
<213> ORGANISM: Artificial
<220> FEATURE:
<223> OTHER INFORMATION: Yeast Expression Vector

<400> SEQUENCE: 13

cctgcagggc ctgaaataac ctctgaaaga ggaacttggt taggtacctt ctgaggcgga     60

aagaaccagc tgtggaatgt gtgtcagtta gggtgtggaa agtccccagg ctccccagca    120

ggcagaagta tgcaaagcat gcatctcaat tagtcagcaa ccaggtgtgg aaagtcccca    180

ggctccccag caggcagaag tatgcaaagc atgcatctca attagtcagc aaccatagtc    240

ccactagtgg agccgagagt aattcataca aaaggaggga tcgccttcgc aaggggagag    300

cccagggacc gtccctaaat tctcacagac ccaaatccct gtagccgccc cacgacagcg    360

cgaggagcat gcgctcaggg ctgagcgcgg ggagagcaga gcacacaagc tcatagaccc    420

tggtcgtggg ggggaggacc ggggagctgg cgcggggcaa actgggaaag cggtgtcgtg    480

tgctggctcc gccctcttcc cgagggtggg ggagaacggt atataagtgc ggcagtcgcc    540

ttggacgttc tttttcgcaa cgggtttgcc gtcagaacgc aggtgagggg cgggtgtggc    600

ttccgcgggc cgccgagctg gaggtcctgc tccgagcggg ccgggccccg ctgtcgtcgg    660

cggggattag ctgcgagcat tcccgcttcg agttgcgggc ggcgcgggag gcagagtgcg    720

aggcctagcg gcaaccccgt agcctcgcct cgtgtccggc ttgaggccta gcgtggtgtc    780

cgcgccgccg ccgcgtgcta ctccggccgc actctggtct tttttttttt tgttgttgtt    840

gccctgctgc cttcgattgc cgttcagcaa taggggctaa caaagggagg gtgcggggct    900

tgctcgcccg gagcccggag aggtcatggt tggggaggaa tggagggaca ggagtggcgg    960

ctggggcccg cccgccttcg gagcacatgt ccgacgccac ctggatgggg cgaggcctgg   1020

ggtttttccc gaagcaacca ggctggggtt agcgtgccga ggccatgtgg ccccagcacc   1080

cggcacgatc tggcttggcg gcgccgcgtt gccctgcctc cctaactagg gtgaggccat   1140

cccgtccggc accagttgcg tgcgtggaaa gatggccgct cccgggccct gttgcaagga   1200

gctcaaaatg gaggacgcgg cagcccggtg gagcgggcgg gtgagtcacc cacacaaagg   1260

aagagggcct ggtccctcac cggctgctgc ttcctgtgac cccgtggtcc tatcggccgc   1320

aatagtcacc tcgggctttt gagcacggct agtcgcggcg gggggagggg atgtaatggc   1380

gttggagttt gttcacattt ggtgggtgga gactagtcag gccagcctgg cgctggaagt   1440

catttttgga atttgtcccc ttgagttttg agcggagcta attctcgggc ttcttagcgg   1500

ttcaaaggta tcttttaaac cctttttttag gtgttgtgaa aaccaccgct aattcaaagc   1560

aaccgggatg ggatggtcat gtatcatcct ttttctagta gcaactgcaa ccggtgtaca   1620

ttctgaggtt cagctggtgg aatcaggtgg tggtctggtt cagccaggag gctctctccg   1680

cttgtcgtgt gctgcttcgg ggtatgactt cacccactat gggatgaatt gggtacgtca   1740
```

```
agcacctggc aaaggacttg agtgggtagg ctggattaac acctatacag gtgaaccgac   1800
ctatgccgca gactttaaac gccgctttac gttttccctg gataccagca agagtacggc   1860
gtatctgcag atgaacagct tacgtgcgga agatacggcg gtctattact gcgccaaata   1920
cccgtactac tatggcacta gccattggta cttcgatgtg tggggtcaag gcactctggt   1980
caccgtgtcc tcagcgtcga ccaagggccc atcggtcttc cccctggcac cctcctccaa   2040
gagcacctct gggggcacag cggccctggg ctgcctggtc aaggactact tccccgaacc   2100
tgtgacggtc tcgtggaact caggcgccct gaccagcggc gtgcacacct tcccggctgt   2160
cctacagtcc tcaggactct actccctcag cagcgtggtg accgtgccct ccagcagctt   2220
gggcacccag acctacatct gcaacgtgaa tcacaagccc agcaacacca aggtggacaa   2280
gaaagttgag cccaaatctt gtgacaaaac tcaccaccac caccaccaca ccggtggtgg   2340
cggcggttct ggaggtggcg gttctggagg cggtggctct gtgcagctgg tggagtctgg   2400
gggaggattg gtgcaggctg gggctctct gagactctcc tgtgcaacct ctggacacac    2460
cttcagtttc tacggcatgg cctggttccg ccaggctcca gggaaggagc gtgagtttgt   2520
agcagccctt agctggagga ctggtagtag ttactatgca gactccgtga agggccgatt   2580
caccatctcc ggagacaacg ccaagaatat gttgtatctg caaatgaaca gcctgaaacc   2640
tgaggacacg gccgtttatt actgtgcagc accagaaaga acgaagttac tacaattaag   2700
actacaaggg gactatgcct actggggcca ggggacccag gtcaccgtct cctcatgaag   2760
atcttgtaca gctagctggc cagacatgat aagatacatt gatgagtttg gacaaaccac   2820
aactagaatg cagtgaaaaa aatgctttat ttgtgaaatt tgtgatgcta ttgctttatt   2880
tgtaaccatt ataagctgca ataaacaagt taacaacaac aattgcattc attttatgtt   2940
tcaggttcag ggggaggtgt gggaggtttt ttaaagcaag taaaacctct acaaatgtgg   3000
tatggaaatg ttaattaact agccatgacc aaaatccctt aacgtgagtt ttcgttccac   3060
tgagcgtcag accccgtaga aaagatcaaa ggatcttctt gagatccttt ttttctgcgc   3120
gtaatctgct gcttgcaaac aaaaaaacca ccgctaccag cggtggtttg tttgccggat   3180
caagagctac caactctttt tccgaaggta actggcttca gcagagcgca gataccaaat   3240
actgttcttc tagtgtagcc gtagttaggc caccacttca agaactctgt agcaccgcct   3300
acatacctcg ctctgctaat cctgttacca gtggctgctg ccagtggcga taagtcgtgt   3360
cttaccgggt tggactcaag acgatagtta ccggataagg cgcagcggtc gggctgaacg   3420
gggggttcgt gcacacagcc cagcttggag cgaacgacct acaccgaact gagataccta   3480
cagcgtgagc tatgagaaag cgccacgctt cccgaaggga gaaaggcgga caggtatccg   3540
gtaagcggca gggtcggaac aggagagcgc acgagggagc ttccaggggg aaacgcctgg   3600
tatctttata gtcctgtcgg gtttcgccac ctctgacttg agcgtcgatt tttgtgatgc   3660
tcgtcagggg ggcggagcct atggaaaaac gccagcaacg cggccttttt acggttcctg   3720
gccttttgct ggccttttgc tcacatgttc ttaattaacc tgcaggcgtt acataactta   3780
cggtaaatgg cccgcctggc tgaccgccca acgacccccg cccattgacg tcaataatga   3840
cgtatgttcc catagtaacg ccaataggga ctttccattg acgtcaatgg gtggagtatt   3900
tacggtaaac tgcccacttg gcagtacatc aagtgtatca tatgccaagt acgcccccta   3960
ttgacgtcaa tgacggtaaa tggcccgcct ggcattatgc ccagtacatg accttatggg   4020
actttcctac ttggcagtac atctacgtat tagtcatcgc tattaccatg atgatgcggt   4080
```

-continued

```
tttggcagta catcaatggg cgtggatagc ggtttgactc acggggattt ccaagtctcc   4140

accccattga cgtcaatggg agtttgtttt gactagtgga gccgagagta attcatacaa   4200

aaggagggat cgccttcgca aggggagagc ccagggaccg tccctaaatt ctcacagacc   4260

caaatccctg tagccgcccc acgacagcgc gaggagcatg cgcccagggc tgagcgcggg   4320

tagatcagag cacacaagct cacagtcccc ggcggtgggg ggaggggcgc gctgagcggg   4380

ggccagggag ctggcgcggg gcaaactggg aaagtggtgt cgtgtgctgg ctccgccctc   4440

ttcccgaggg tgggggagaa cggtatataa gtgcggtagt cgccttggac gttctttttc   4500

gcaacgggtt tgccgtcaga acgcaggtga gtggcgggtg tggcttccgc gggccccgga   4560

gctggagccc tgctctgagc gggccgggct gatatgcgag tgtcgtccgc agggtttagc   4620

tgtgagcatt cccacttcga gtggcgggcg gtgcgggggt gagagtgcga ggcctagcgg   4680

caaccccgta gcctcgcctc gtgtccggct tgaggcctag cgtggtgtcc gccgccgcgt   4740

gccactccgg ccgcactatg cgtttttttgt ccttgctgcc ctcgattgcc ttccagcagc   4800

atgggctaac aaagggaggg tgtggggctc actcttaagg agcccatgaa gcttacgttg   4860

gataggaatg gaagggcagg aggggcgact ggggcccgcc cgccttcgga gcacatgtcc   4920

gacgccacct ggatggggcg aggcctgtgg ctttccgaag caatcgggcg tgagtttagc   4980

ctacctgggc catgtggccc tagcactggg cacggtctgg cctggcggtg ccgcgttccc   5040

ttgcctccca acaagggtga ggccgtcccg cccggcacca gttgcttgcg cggaaagatg   5100

gccgctcccg gggccctgtt gcaaggagct caaaatggag gacgcggcag cccggtggag   5160

cgggcgggtg agtcacccac acaaaggaag agggccttgc ccctcgccgg ccgctgcttc   5220

ctgtgacccc gtggtctatc ggccgcatag tcacctcggg cttctcttga gcaccgctcg   5280

tcgcggcggg gggaggggat ctaatggcgt tggagtttgt tcacatttgg tgggtggaga   5340

ctagtcaggc cagcctggcg ctggaagtca ttcttggaat ttgccccttt gagtttggag   5400

cgaggctaat tctcaagcct cttagcggtt caaaggtatt ttctaaaccc gtttccaggt   5460

gttgtgaaag ccaccgctaa ttcaaagcaa tccggagtat acggatctat ggactggacc   5520

tggaggattc tcttcttggt ggcggccgcc acaggcgcgc actccgacat tcagctgact   5580

cagagtcctt ccagcttaag cgcatctgtt ggcgatcgtg tgacgattac gtgtagtgcc   5640

tcgcaagaca tctccaacta cctgaattgg tatcagcaga aaccgggcaa agctccgaaa   5700

gtcctgatct acttcacctc atcgctgcat agcggtgtac caagtcgctt tagcggttct   5760

ggctcaggta ccgatttcac cctcacgatt agctcgttgc aacccgaaga ttttgcgacc   5820

tattactgcc agcagtattc cactgttccg tggacctttg gacaagggac aaaggtggag   5880

atcaaacgta cggtggctgc accatctgtc ttcatcttcc cgccatctga tgagcagttg   5940

aaatctggaa ctgcctctgt tgtgtgcctg ctgaataact tctatcccag agaggccaaa   6000

gtacagtgga aggtggataa cgccctccaa tcgggtaact cccaggagag tgtcacagag   6060

caggacagca aggacagcac ctacagcctc agcagcaccc tgacgctgag caaagcagac   6120

tacgagaaac acaaagtcta cgcctgcgaa gtcacccatc agggcctgag ctcgcccgtc   6180

acaaagagct tcaacagggg agagtgttaa cctaggagca ggtttcccca atgacacaaa   6240

acgtgcaact tgaaactccg cctggtcttt ccaggtctag aggggtaaca ctttgtactg   6300
```

-continued

```
cgtttggctc cacgctcgat ccactggcga gtgttagtaa cagcactgtt gcttcgtagc   6360
ggagcatgac ggccgtggga actcctcctt ggtaacaagg acccacgggg ccaaaagcca   6420
cgcccacacg ggcccgtcat gtgtgcaacc ccagcacggc gactttactg cgaaacccac   6480
tttaaagtga cattgaaact ggtacccaca cactggtgac aggctaagga tgcccttcag   6540
gtaccccgag gtaacacgcg acactcggga tctgagaagg ggactggggc ttctataaaa   6600
gcgctcggtt taaaaagctt ctatgcctga ataggtgacc ggaggtcggc acctttcctt   6660
tgcaattact gaccctatga atacactgac tgtttgacaa ttaatcatcg gcatagtata   6720
tcggcatagt ataatacgac tcactatagg agggccacca tgaagaaacc tgaactgaca   6780
gcaacttctg ttgagaagtt tctcattgaa aaatttgatt ctgtttctga tctcatgcag   6840
ctgtctgaag gtgaagaaag cagagccttt tcttttgatg ttggaggaag aggttatgtt   6900
ctgagggtca attcttgtgc tgatggtttt tacaaagaca gatatgttta cagacacttt   6960
gcctctgctg ctctgccaat tccagaagtt ctggacattg gagaattttc tgaatctctc   7020
acctactgca tcagcagaag agcacaagga gtcactctcc aggatctccc tgaaactgag   7080
ctgccagctg ttctgcaacc tgttgctgaa gcaatggatg ccattgcagc agctgatctg   7140
agccaaacct ctggatttgg tccttttggt ccccaaggca ttggtcagta caccacttgg   7200
agggatttca tttgtgccat tgctgatcct catgtctatc actggcagac tgtgatggat   7260
gacacagttt ctgcttctgt tgctcaggca ctggatgaac tcatgctgtg ggcagaagat   7320
tgtcctgaag tcagacacct ggtccatgct gattttggaa gcaacaatgt tctgacagac   7380
aatggcagaa tcactgcagt cattgactgg tctgaagcca tgtttggaga ttctcaatat   7440
gaggttgcca acattttttt ttggagacct tggctggctt gcatggaaca acaaacaaga   7500
tattttgaaa gaagacaccc agaactggct ggttccccca gactgagagc ctacatgctc   7560
agaattggcc tggaccaact gtatcaatct ctggttgatg gaaactttga tgatgctgct   7620
tgggcacaag gaagatgtga tgccattgtg aggtctggtg ctggaactgt tggaagaact   7680
caaattgcaa gaaggtctgc tgctgtttgg actgatggat gtgttgaagt tctggctgac   7740
tctggaaaca ggagaccctc cacaagaccc agagccaagg aaatggtgag caagggcgag   7800
gagctgttca ccggggtggt gcccatcctg gtcgagctgg acggcgacgt aaacggccac   7860
aagttcagcg tgtccggcga gggcgagggc gatgccacct acggcaagct gaccctgaag   7920
ttcatctgca ccaccggcaa gctgcccgtg ccctggccca ccctcgtgac caccctgacc   7980
tacggcgtgc agtgcttcag ccgctacccc gaccacatga agcagcacga cttcttcaag   8040
tccgccatgc ccgaaggcta cgtccaggag cgcaccatct tcttcaagga cgacggcaac   8100
tacaagaccc gcgccgaggt gaagttcgag ggcgacaccc tggtgaaccg catcgagctg   8160
aagggcatcg acttcaagga ggacggcaac atcctggggc acaagctgga gtacaactac   8220
aacagccaca acgtctatat catggccgac aagcagaaga acggcatcaa ggtgaacttc   8280
aagatccgcc acaacatcga ggacggcagc gtgcagctcg ccgaccacta ccagcagaac   8340
acccccatcg gcgacggccc cgtgctgctg cccgacaacc actacctgag cacccagtcc   8400
gccctgagca aagaccccaa cgagaagcgc gatcacatgg tcctgctgga gttcgtgacc   8460
gccgccggga tcactctcgg catggacgag ctgtacaagt gaatattagg cctgaaaggc   8520
cgctagatta tccctaatac ctgccacccc actcttaatc agtggtggaa gaacggtctc   8580
agaactgttt gtttcaattg gccatttaag tttagtagta aaagactggt taatgataac   8640
aatgcatcgt aaaaccttca gaaggaaagg agaatgtttt gtggaccact ttggttttct   8700
```

-continued

```
tttttgcgtg tggcagtttt aagttattag tttttaaaat cagtactttt taatggaaac   8760

aacttgacca aaaatttgtc acagaatttt gagacccatt aaaaaagtta aatgagaaac   8820

ctgtgtgttc ctttggtcaa caccgagaca tttaggtgaa agacatctaa ttctggtttt   8880

acgaatctgg aaacttcttg aaaatgtaat tcttgagtta acacttctgg gtggagaata   8940

gggttgtttt ccccccacat aattggaagg ggaaggaata tcatttaaag ctatgggagg   9000

gttgctttga ttacaacact ggagagaaat gcagcatgtt gctgattgcc tgtcactaaa   9060

acaggccaaa aactgagtcc ttgggttgca tagaaagctg                         9100
```